US005629304A

United States Patent [19]

Murakata et al.

[11] Patent Number: 5,629,304

[45] Date of Patent: May 13, 1997

[54] THERAPEUTIC AGENT FOR THROMBOCYTOPENIA AND INDOLOCARBAZOLE DERIVATIVES

[75] Inventors: Chikara Murakata, Hachioji; Fumihiko Kanai; Yutaka Saitoh, both of Machida; Yukimasa Shiotsu, Tokyo; Takako Shiraki; Tatsuya Tamaoki, both of Machida; Shiro Akinaga, Sunto-gun; Masami Okabe, Mishima, all of Japan

[73] Assignee: Kyowa Hakko Kogyo Co., Ltd., Tokyo, Japan

[21] Appl. No.: 637,590

[22] Filed: Apr. 25, 1996

Related U.S. Application Data

[63] Continuation of Ser. No. 404,962, Mar. 16, 1995, abandoned.

[30] Foreign Application Priority Data

Mar. 18, 1994 [JP] Japan .................................... 6-049579

[51] Int. Cl.$^6$ ........................ A61K 31/40; C07D 487/12

[52] U.S. Cl. ......................... 514/183; 514/410; 514/424; 548/417

[58] Field of Search .................................... 514/410, 424, 514/183; 548/417

[56] References Cited

U.S. PATENT DOCUMENTS

| | | | |
|---|---|---|---|
| 4,923,986 | 5/1990 | Murakata et al. | 540/545 |
| 5,073,633 | 12/1991 | Schroeder et al. | 540/545 |
| 5,438,050 | 8/1995 | Kleinschroth et al. | 548/417 |
| 5,468,872 | 11/1995 | Glicksman et al. | 548/416 |

FOREIGN PATENT DOCUMENTS

| | | |
|---|---|---|
| 0630898 | 12/1994 | European Pat. Off. . |
| WO13071 | 9/1991 | WIPO . |
| WO18766 | 9/1993 | WIPO . |
| WO18765 | 9/1993 | WIPO . |

OTHER PUBLICATIONS

Patent Abstracts of Japan, vol. 118, No. 28 (1993) 102001y.
Tetrahedron Letters, vol. 35, No. 49 (1994) pp. 9135–9138.
Hidaka et al., Ann. Rev. Pharmacol. Toxicol., vol. 32 (1992) 377:97.

*Primary Examiner*—Mukund J. Shah
*Assistant Examiner*—Pavanaram K. Sripada
*Attorney, Agent, or Firm*—Fitzpatrick, Cella, Harper & Scinto

[57] ABSTRACT

The present invention provides a method of treating thrombocytopenia, which comprises administering to a patient suffering from thrombocytopenia, an effective amount of an indolocarbazole derivative represented by formula (I):

(I)

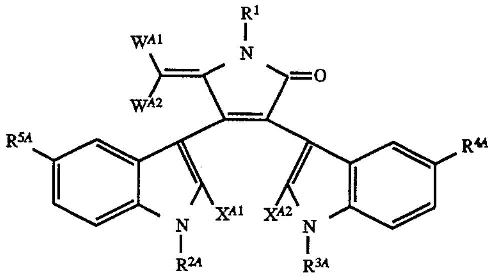

wherein $R^1$ represents a hydrogen atom, a substituted or unsubstituted lower alkyl group, a substituted or unsubstituted aralkyl group or a tetrahydropyranyl group; $R^{2A}$ and $R^{3A}$, which may be the same or different, each represent a hydrogen atom, a substituted or unsubstituted lower alkyl group, a lower alkenyl group, a substituted or unsubstituted aralkyl group or a monosaccharide residue where a hydroxyl group at the anomer position is removed; $R^{4A}$ and $R^{5A}$, which may be the same or different, each represent a hydrogen atom, a formyl group, a hydroxyl group or a halogen atom; $W^{A1}$ and $W^{A2}$ represent hydrogen atoms or are combined together to form an oxygen atom; and $X^{A1}$ and $X^{A2}$ represents two hydrogen atoms or are combined together to form a single bond, provided that when $X^A$ forms a single bond, then $R^1$, $R^{2A}$, $R^{3A}$, $R^{4A}$, $R^{5A}$, and $W^A$ do not simultaneously represent a hydrogen atom, or a pharmaceutically acceptable salt.

7 Claims, No Drawings

THERAPEUTIC AGENT FOR THROMBOCYTOPENIA AND INDOLOCARBAZOLE DERIVATIVES

This application is a continuation of Application Ser. No. 08/404,962, filed Mar. 16, 1995, now abandoned.

BACKGROUND OF THE INVENTION

The present invention relates to a method of treating thrombocytopenia and a novel indolocarbazole derivative useful as a therapeutic agent for thrombocytopenia. A therapeutic agent for thrombocytopenia is expected to be useful for the treatment of the decrease of blood platelets in number which is a side effect of chemotherapy for cancer and transplantation of bone marrow and for various diseases involving thrombocytopenia.

Decrease of blood platelets in number due to various hematopoietic disorders causes serious symptoms including an increased tendency to hemorrhage. At present, platelet transfusion is considered to be effective against decrease of blood platelets, but an ample amount of blood platelets is not always supplied.

Known hematopoietic factors which stimulate the production of blood platelets include interleukin (IL) 6 and IL 11 (see *Blood*, 75, 1602 (1990), ibid, 81, 901 (1993)).

Indolocarbozole derivatives having two glycosidic inkages are known to have inhibitory activity against a variety of protein kinase, such as protein kinase C, antitumor activity (see Japanese Published Unexamined Patent Application Nos. 220196/87 (U.S. Pat. No. 4,935,415), 168689/89 (U.S. Pat. No. 4,877,776), WO 88-07045 (U.S. Pat. No. 4,923,986) and WO 89-07105 (EP 383919A)), inhibitory activity against blood platelet agglutination (see Japanese Published Unexamined Patent Application No. 364186/92) or vasodilating activity (see Japanese Published Unexamined Patent Application No. 143877/89) .

Indolocarbozole derivatives with one or no glycosidic linkage are known to have protein kinase C inhibitory activity (see Japanese Published Unexamined Patent Application Nos. 149520/90 (EP 328000A), 294279/91 (EP 434057A) and 174778/90 (EP 370236A), and WO 93-24491), antitumor activity (see WO 93-11145 (EP 545195A)), antiviral activity (see WO 93-18766) , or antithrombotic and antiallergic activity (see Japanese Published Unexamined Patent Application No. 294279/91 (EP 434057A)).

However, it is unknown that indolocarbazole derivatives of either type exhibit stimulating activity on blood platelet production.

SUMMARY OF THE INVENTION

An object of the present invention is to provide a method of treating thrombocytopenia, which comprises administering to a patient suffering from thrombocytopenia an effective amount of an indolocarbazole derivative.

Another object of the present invention is to provide a novel indolocarbazole derivative useful as a therapeutic agent for thrombocytopenia.

The present invention provides a method of treating thrombocytopenia which comprises administering to a patient suffering from thrombocytopenia an effective amount of an indolocarbazole derivative represented by formula (I):

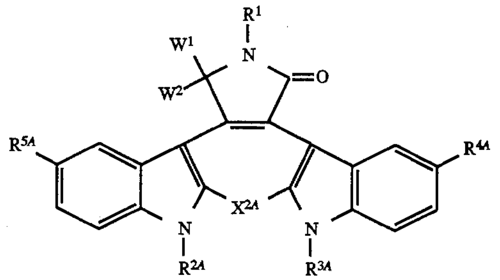

(I)

wherein $R^1$ represents a hydrogen atom, a substituted or unsubstituted lower alkyl group, a substituted or unsubstituted aralkyl group or a tetrahydropyranyl group; $R^{2A}$ and $R^{3A}$, which may be the same or different, each represent a hydrogen atom, a substituted or unsubstituted lower alkyl group, a lower alkenyl group, a substituted or unsubstituted aralkyl group or a monosaccharide residue where a hydroxyl group at the anomer position is removed; $R^{4A}$ and $R^{5A}$, which may be the same or different, each represent a hydrogen atom, a formyl group, a hydroxyl group or a halogen atom; $W^{A1}$ and $W^{A2}$ are both hydrogen atom or are combined together to represent an oxygen atom; and $X^{1A}$ and $X^{2A}$ each represents a hydrogen atom or are combined together to form a single bond, provided that when $X^{1A}$ and $X^{2A}$ form forms a single bond, then $R^1$, $R^{2A}$, $R^{3A}$, $R^{4A}$, $R^{5A}$, and $W^{A1}$ and $W^{A2}$ do not simultaneously represent a hydrogen atom, (hereinafter referred to as Compound (I)) or a pharmaceutically acceptable salt thereof.

The present invention also provides an indolocarbazole derivative represented by formula (II):

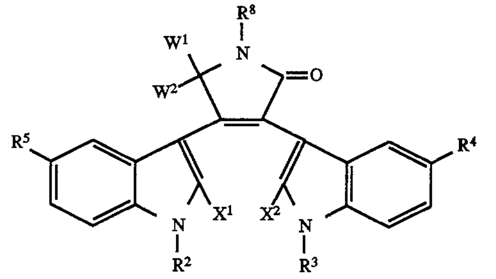

(II)

wherein $R^8$ represents a substituted or unsubstituted lower alkyl group, a substituted or unsubstituted aralkyl group or a tetrahydropyranyl group; $R^2$ and $R^3$, which may be the same or different, each represent a hydrogen atom, a substituted or unsubstituted lower alkyl group, a lower alkenyl group, a substituted or unsubstituted aralkyl group or a monosaccharide residue where a hydroxyl group at the anomer position is removed; $R^4$ and $R^5$, which may be the same or different, each represent a hydrogen atom, a formyl group, a hydroxyl group or a halogen atom; $W^1$ and $W^2$ are both hydrogen or are combined together to represent an oxygen atom; and $X^1$ and $X^2$ each represent a hydrogen atom or are combined together to form a single bond; provided that $R^2$ and $R^3$ do not simultaneously represent a hydrogen atom, and also provided that when $R^2$ and $R^3$, which may be the same or different, each represent an allyl group or $CH_2CH(OH)CH_2OH$, then $R^8$ is not a methyl group and $W^1$ and $W^2$ are not combined to form an oxygen atom, (hereinafter referred to as Compound (II)) or a pharmaceutically acceptable salt thereof.

Likewise, the same numbering shall apply to compounds with other formula numbers.

DETAILED DESCRIPTION OF THE INVENTION

In Compounds (I) and (II), the lower alkyl group means a straight-chain or branched alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl or hexyl. The substituent(s) in the substituted lower alkyl group is/are 1 to 3 groups, which may be the same or different, selected from a hydroxyl group, a formyloxy group, a halogen atom, a lower alkoxycarbonyl group, a carboxyl group, a guanidido group, an imidazolyl group, an azido group, and $NR^6R^7$ (wherein $R^6$ and $R^7$, which may be the same or different, each represent a hydrogen atom, a lower alkyl group (which may be substituted with 1 to 3 same or different substituents selected from a hydroxyl group, a formyloxy group, a halogen atom, a carboxyl group, and an amino group) or a cycloalkyl group, or $R^6$ and $R^7$ are taken together with N to form a heterocyclic group (which may contain an oxygen atom, a sulfur atom and/or an additional nitrogen atom). The alkyl moiety of the lower alkoxycarbonyl group and the lower alkyl group in $R^6$ and $R^7$ have the same meaning as the above-mentioned lower alkyl group. The halogen atom in the substituents on the lower alkyl group includes chlorine, bromine and iodine. The cycloalkyl group includes cycloalkyl groups having 3 to 8 carbon atoms, such as cyclopropyl, cyclobutyl, cyclopentyl, cyclohexyl, and cyclooctyl groups. The N-containing heterocyclic group formed by $R^6$ and $R^7$ includes pyrrolidinyl, morpholino, thiomorpholino, N-methylpiperazinyl, pyrazolidinyl, piperidino, piperazinyl, indolyl, isoindolyl and the like. The lower alkenyl group means an alkenyl group having 2 to 6 carbon atoms, such as vinyl, allyl, butenyl, pentenyl, hexenyl, pentadienyl or hexadienyl. The aralkyl group means an aralkyl group having 7 to 15 carbon atoms, such as benzyl, phenethyl, benzhydryl and naphthylmethyl. The substituent(s) in the substituted aralkyl group is/are 1 to 3 groups selected from a nitro group, an amino group, a lower alkylamino group, and a di(lower alkyl)amino group. The lower alkyl moiety in the lower alkylamino or di(lower alkyl)amino group has the same meaning as the above-mentioned lower alkyl group.

The monosaccharide includes hexoses and pentoses, such as glucose, mannose, and galactose.

The halogen atom includes fluorine, chlorine, bromine and iodine atoms.

The "single bond" in the definition of $X^1$ and $X^2$ means a covalent bond between the two carbon atoms each adjacent to the nitrogen of each carbazole skeleton.

The pharmaceutically acceptable salts of Compounds (I) and (II) include acid addition salts, metal salts, ammonium salts, organic amine addition salts, and amino acid addition salts. The acid addition salts include those with inorganic acids, such as a hydrochloride, a sulfate and a phosphate; and those with organic acids, such as an acetate, a maleate, a fumarate, a tartrate, a citrate, a lactate, an aspartate, and a glutamate. The metal salts include those with an alkali metal, such as a sodium salt and a potassium salt; those with an alkaline earth metal, such as a magnesium salt and a calcium salt; aluminum salts, and zinc salts. The ammonium salts include a salt with ammonium or tetramethylammonium. The organic amine addition salts include those with morpholine or piperidine, and the amino acid addition salts include those with lysine, glycine or phenylalanine.

Compounds (II) can be prepared by, for example, processes (1) to (4) described below. In the following structural formulae, tables, etc., symbols Me, Et, Pr, i-Pr, Hex, allyl, Bn, and THP stand for methyl, ethyl, propyl, isopropyl, hexyl, allyl, benzyl, and tetrahydropyranyl, respectively.

In the following processes, where a group as specified undergo change under practical conditions or is improper for carrying out the process, a protective group can be introduced and then cleaved in a manner commonly employed in organic synthetic chemistry (see, for example, T. W. Greene, *Protective Groups in Organic Synthesis*, John wiley & Sons Inc. (1981)). If desired, the order of introducing substituents may be changed.

Process 1:

Compound (II) can be prepared by the following reaction steps.

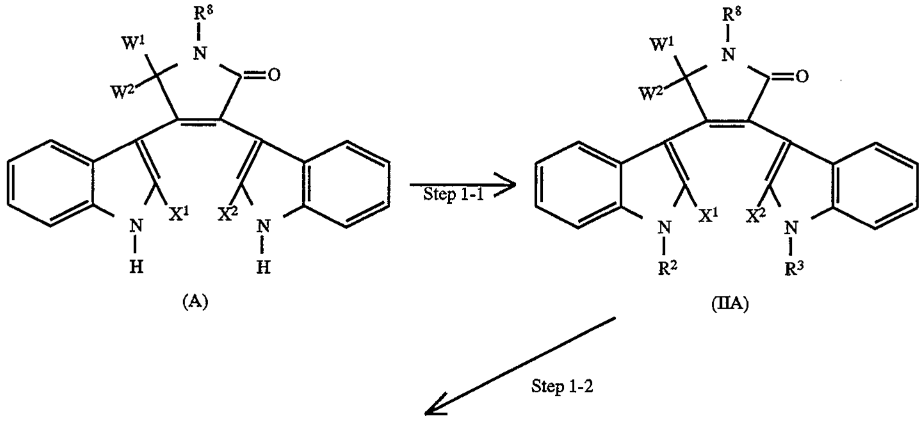

(A)

(IIA)

-continued

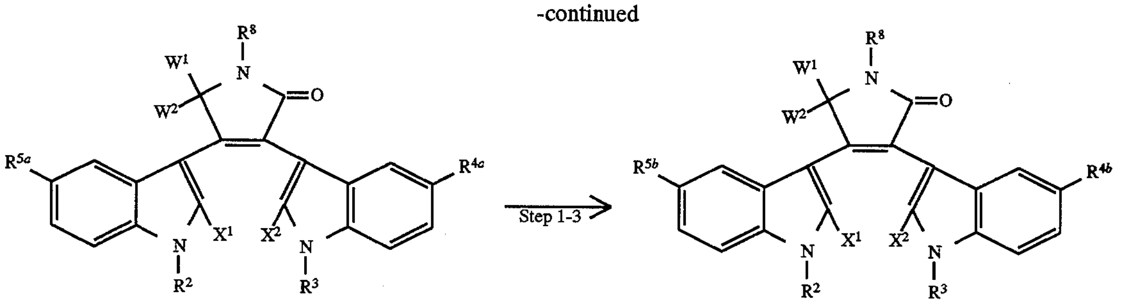

(IIB) (IIC)

wherein $R^2$, $R^3$, $R^8$, $W^1$, $W^2$, $W^1$ and $X^2$ are as defined above; at least one of $R^{4a}$ and $R^{5a}$ represents a formyl group or a halogen atom; and at least one of $R^{4b}$ and $R^{5b}$ represents a hydroxyl group.

Step 1-1:

Compound (A), which is obtained by a known process (e.g., *J Chem. Soc. Perkin Trans I*, 2475 (1990), *Tetrahedron Lett.*, 34, 5329 (1993), or *Tetrahedron*, 44, 2887 (1988)), is reacted with a compound represented by formula (III):

$R^9Hal$ (III)

wherein $R^9$ means all the groups but hydrogen in the definition of $R^2$ or $R^3$; and Hal represents chlorine, bromine or iodine, in an inert solvent in the presence of a base to give Compound (IIA).

The reaction solvent to be used includes N,N-dimethylformamide (DMF), tetrahydrofuran (THF), toluene, and a mixture thereof. The base to be used includes sodium hydride and potassium tert-butoxide. Compound (III) and the base are each used in an amount of from 1 to 6 equivalents based on Compound (A). The reaction is carried out at −20° to 50° C. for 1 to 24 hours.

Step 1-2-1:

Compound (IIA) is reacted with dichloromethyl methyl ether in an inert solvent in the presence of a Lewis acid to give Compound (IIB-1) which is Compound (IIB) in which at east one of $R^{4a}$ and $R^{5a}$ is a formyl group.

Useful reaction solvent includes methylene chloride, chloroform, and 1,2-dichloroethane. Suitable Lewis acid includes titanium tetrachloride. The Lewis acid and dichloromethyl methyl ether are each used in an amount of from 1 to 10 equivalents based on Compound (IIA). The reaction is carried out at −10° to 80° C. for 1 to 8 hours.

Step 1-2-2:

Compound (IIA) is reacted with a halogenating reagent, such as an N-halogenated succinimide, in an inert solvent to give Compound (IIB-2), which is Compound (IIB) in which at least one of $R^{4a}$ and $R^{5a}$ is a halogen atom.

Suitable reaction solvents include chloroform and THF. The halogenating reagent is used in an amount of from 3 to 5 equivalents based on Compound (IIA). The reaction is carried out at 0° to 50° C. for 3 to 24 hours.

Step 1-3:

Compound (IIB-1) is reacted with a peroxide in an inert solvent in the presence of a base to give a formic ester, which is then subjected to alkali hydrolysis to give Compound (IIC).

The reaction solvent to be used in the esterification includes methylene chloride, chloroform, and 1,2-dichloroethane. Useful peroxides include m-chloroperbenzoic acid, peracetic acid, aqueous hydrogen peroxide, and t-butyl hydroperoxide. Useful bases include sodium hydrogencarbonate, sodium carbonate, potassium hydrogencarbonate, potassium carbonate, and sodium acetate. The peroxide and the base are each used in an amount of from 1 to 20 equivalents based on Compound (IIB-1). The reaction is performed at −10° to 80° C. for 5 to 72 hours. The resulting ester can be subjected to the subsequent hydrolysis without being purified.

Suitable reaction solvents to be used in the alkali hydrolysis of the ester include mixed solvents of water-containing methanol with methylene chloride, chloroform or 1,2-dichloroethane. Useful alkalis include sodium methoxide, sodium hydrogencarbonate, potassium carbonate, and aqueous ammonia. The alkali is used in an amount of from 0.5 to 2 equivalents based on the ester. The reaction is effected at −10° to 50° C. for 10 minutes to 5 hours.

Process 2:

Compound (IIE) which is Compound (II) with its substituent $R^8$ varied, as represented by formula (IIE), can also be prepared from Compound (IID) in which $R^8$ is tetrahydropyranyl (THP), as represented by formula (IID), via Compound (B).

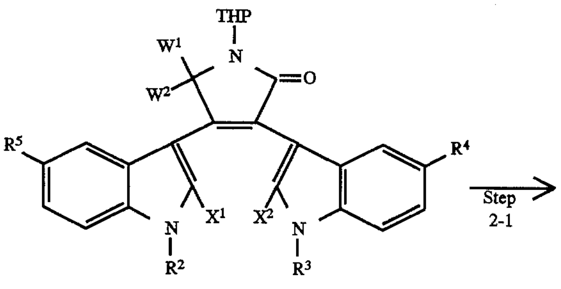

(IID)

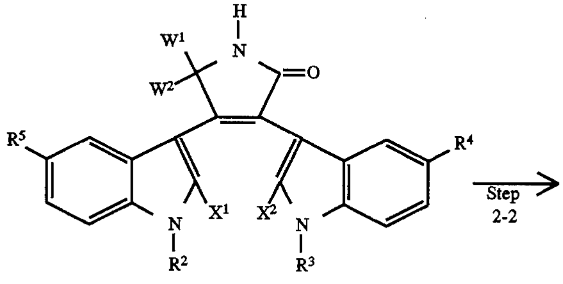

(B)

-continued

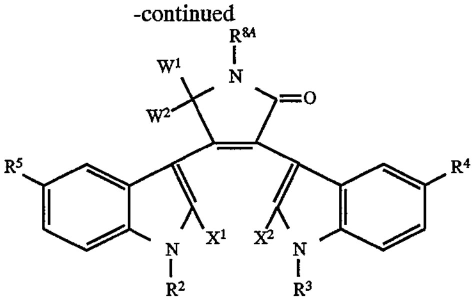

(IIE)

wherein $R^2$, $R^3$, $R^4$, $R^5$, $W^1$, $W^2$, $X^1$ and $X^2$ are as defined above; and $R^{8a}$ represents the same groups as defined for $R^8$ except for a tetrahydropyranyl group.

Step 2-1:

Compound (IID) is treated with an acid, such as 4N sulfuric acid, in a solvent, such as THF, to give Compound (B). The acid is used in an amount of from 20 to 100% by volume based on the solvent. The reaction is conducted at 30° to 80° C. for 3 to 24 hours.

Step 2-2:

Compound (B) is reacted with Compound (IV) represented by formula:

$R^{8a}Hal$ (IV)

wherein $R^{8a}$ and Hal are as defined above, in an inert solvent in the presence of a base to give Compound (IIE).

Useful reaction solvents include DMF, THF, toluene, or a mixture thereof. Useful bases include sodium hydride and potassium tert-butoxide. Compound (IV) and the base are each used in an amount of from 1 to 3 equivalents based on Compound (B). The reaction is carried out at −10° to 50° C. for 1 to 24 hours.

Process 3:

Compound (IIF), which is Compound (II) in which $R^8$ is $-(CH_2)_5OH$, can also be prepared from Compound (IID) obtained by process 1.

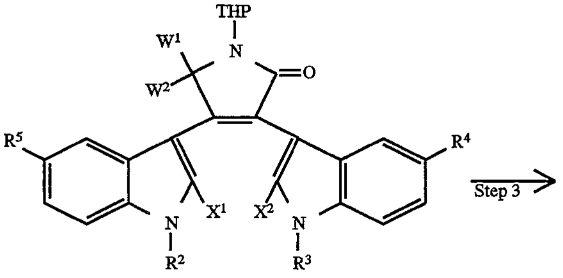

(IID)

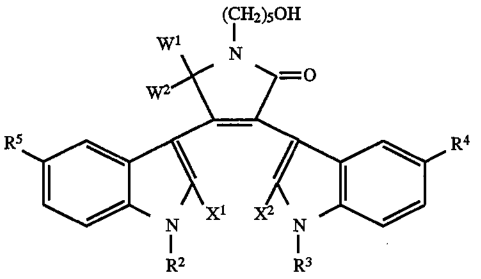

(IIF)

wherein $R^2$, $R^3$, $R^4$, $R^5$, $W^1$, $W^2$, $X^1$ and $X^2$ are as defined above Step 3:

Compound (IID) is reduced in a solvent, such as THF, in the presence of a reducing agent, such as borane prepared from sodium borohydride and iodine, to give Compound (IIF). Sodium borohydride and iodine are used in an amount of from 7 to 16 equivalents and from 3 to 5 equivalents, respectively, based on Compound (IID). The reaction is conducted at −10° to 50° C. for 1 to 24 hours.

Process 4:

Compound (II) having a functional group at $R^2$ and $R^3$, as represented by formula (IIH), can also be prepared from the compound obtained in process 1 or 2 and having a different functional group at $R^2$ and $R^3$, as represented by formula (IIG), in accordance with the following steps 4-1 to 4-10.

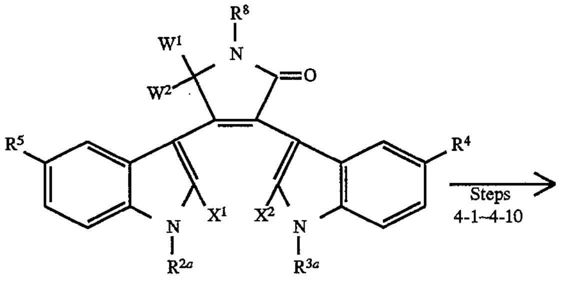

(IIG)

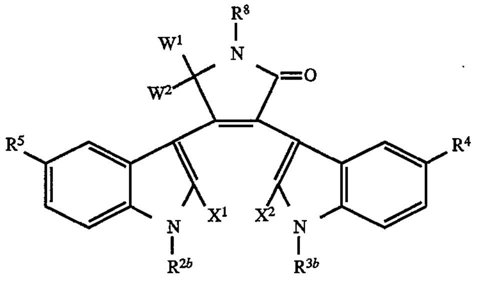

(IIH)

wherein $R^4$, $R^5$, $R^8$, $W^1$, $W^2$, $X^1$ and $X^2$ are as defined above; and the functional groups at $R^{2a}$, $R^{3a}$, $R^{2b}$, and $R^{3b}$ are defined in each of the following steps.

Step 4-1:

In formula (IIG), at least one of $R^{2a}$ and $R^{3a}$ is a lower alkenyl group, and in formula (IIH) at least one of $R^{2b}$ and $R^{3b}$ is a lower alkyl group substituted with one hydroxyl group.

Compound (IIG) is reduced in a solvent, e.g., THF, with a reducing agent, such as borane prepared from sodium borohydride and iodine, to give Compound (IIH). Sodium borohydride and iodine are used in an amount of from 2 to 6 equivalents and from 2 to 3 equivalents, respectively, based on Compound (IIG). The reaction is performed at −10° to 50° C. for 1 to 24 hours.

Compound (IIH) can also be obtained by reacting Compound (IIG) with a reducing agent, such as 9-borabicyclo [3.3.1]nonane (9-BBN), in a solvent, such as THF, and then reacted with a peroxide, such as 35% hydrogen peroxide in the presence of 1N sodium hydroxide. 9-BBN, 1N sodium hydroxide, and 35% hydrogen peroxide are used in an amount of from 5 to 15 equivalents, 2 to 10 equivalents, and 30 to 50 equivalents, respectively, based on Compound (IIG). The reaction is carried out at −10° to 50° C. for 5 to 24 hours.

Step 4-2:

In formula (IIG) at least one of $R^{2a}$ and $R^{3a}$ is a nitro-substituted aralkyl group or an azido-substituted lower alkyl group; and in formula (IIH) at least one of $R^{2b}$ and $R^{3b}$ is an amino-substituted aralkyl group or an amino-substituted lower alkyl group.

Compound (IIG) is catalytically reduced in a solvent, such as THF or DMF, in the presence of a catalyst, such as 20% $Pd(OH)_2/C$ or $PtO_2$, to give Compound (IIH). The catalyst for reduction is used in an amount of 10 to 100% by weight based on Compound (IIG). The reaction is effected at −10° to 50° C. for 30 minutes to 24 hours.

Step 4-3:

In formula (IIG) at least one of $R^{2a}$ and $R^{3a}$ is an amino-substituted aralkyl group or an amino-substituted lower alkyl group; and in formula (IIH), at least one of $R^{2b}$ and $R^{3b}$ is a lower alkylamino-substituted aralkyl group or a lower alkylamino-substituted lower alkyl group.

Compound (IIG) is reacted with aldehyde in a solvent, such as a mixed solvent of THF and methanol, in the presence of sodium cyanoborohydride to give Compound (IIH). Sodium cyanoborohydride and aldehyde are each used in an amount of from 1 to 2 equivalents based on Compound (IIG). The reaction is carried out at −10° to 50° C.

Step 4-4:

In formula (IIG) at least one of $R^{2a}$ and $R^{3a}$ is an amino-substituted aralkyl group or an amino-substituted lower alkyl group and in formula (IIH) at least one of $R^{2b}$ and $R^{3b}$ is a di(lower alkyl)amino-substituted aralkyl group or a di(lower alkyl)amino-substituted lower alkyl group.

Compound (IIG) can be obtained in the same manner as in step 4-3, except for using sodium cyanoborohydride and aldehyde in amounts of 1 to 20 equivalents based on Compound (IIG).

Step 4-5:

In formula (IIG) at least one of $R^{2a}$ and $R^{3a}$ is a lower alkenyl group; and in formula (IIH) at least one of $R^{2b}$ and $R^{3b}$ is a lower alkyl group substituted with two hydroxyl groups.

Compound (IIG) is reacted with osmium tetroxide in a solvent, such as a 10/1 mixed solvent of THF and pyridine, in the presence of morpholine N-oxide to give Compound (IIH). Osmium tetroxide and morpholine N-oxide are used in an amount of from 0.02 to 1 equivalent and from 1 to 5 equivalents, respectively, based on Compound (IIG). The reaction is performed at −10° to 50° C. for 5 to 24 hours.

Step 4-6:

In formula (IIG), at least one of $R^{2a}$ and $R^{3a}$ is a hydroxy-substituted lower alkyl group; and in formula (IIH) at least one of $R^{2b}$ and $R^{3b}$ is a halogen- and/or formyloxy-substituted lower alkyl group.

Compound (IIG) is reacted with triphenylphosphine and a halogen in a solvent, such as DMF, to give Compound (IIH). Triphenylphosphine and the halogen are used in amounts of from 2 to 6 equivalents based on Compound (IIG). The reaction is conducted at −10° to 50° C. for 1 to 24 hours.

Step 4-7:

In formula (IIG) at least one of $R^{2a}$ and $R^{3a}$ is a halogen-substituted lower alkyl group; and in formula (IIH) at least one of $R^{2b}$ and $R^{3b}$ is $NR^6R^7$ or an azido-substituted lower alkyl group.

Compound (IIG) is reacted with $HNR^6R^7$ or sodium azide in a solvent, such as DMF, to give Compound (IIH). $HNR^6R^7$ or sodium azide is used in an amount of from 2 to 10 equivalents based on Compound (IIG). The reaction is conducted at 10° to 120° C. for 1 to 24 hours.

Step 4-8:

In formula (IIG) at least one of $R^{2a}$ and $R^{3a}$ is a halogen-substituted lower alkyl group; and in formula (IIH) at least one of $R^{2b}$ and $R^{3b}$ is an imidazolyl-substituted lower alkyl group.

Compound (IIG) is reacted with imidazole in a solvent, such as DMF, in the presence of sodium hydride to give Compound (IIH). Sodium hydride and imidazole are used in amounts of from 2 to 5 equivalents based on Compound (IIG). The reaction is carried out at −10° to 50° C. for 10 minutes to 5 hours.

Step 4-9:

In formula (IIG) at least one of $R^{2a}$ and $R^{3a}$ is an amino-substituted lower alkyl group; and in formula (IIH) at least one of $R^{2b}$ and $R^{3b}$ is a guanidido-substituted lower alkyl group.

Compound (IIG) is reacted with 3,5-dimethylpyrazole-1-carboxyamidine nitrate in a solvent, such as a 2:3 mixed solvent of DMF and ethanol, in the presence of sodium hydrogencarbonate to give Compound (IIH). Sodium hydrogencarbonate and 3,5-dimethylpyrazole-1-carboxyamidine nitrate are used in amounts of 1 to 2 equivalents based on Compound (IIG). The reaction is conducted at 50° to 130° C. for 1 to 8 hours.

Step 4-10:

In formula (IIG) at least one of $R^{2a}$ and $R^{3a}$ is a lower alkoxycarbonyl-substituted lower alkyl group; and in formula (IIH) at least one of $R^{2b}$ and $R^{3b}$ is a carboxy-substituted lower alkyl group.

Compound (IIG) is hydrolyzed in a solvent, such as a 3:1 mixed solvent of THF and water, with an alkali, such as lithium hydroxide or sodium hydroxide, to give Compound (IIH). The alkali is used in an amount of from 1 to 5 equivalents based on Compound (IIG). The reaction is performed at 0° to 50° C. for 1 to 24 hours.

In addition to the above-described steps, conversion of functional groups as $R^2$, $R^3$, $R^4$, $R^5$ and $R^8$ can be effected by other known techniques, such as the process described in R. C. Larock, *Comprehensive Organic Transformations* (1989).

The product obtained by the above-described processes can be isolated and purified by methods commonly employed in organic syntheses, such as filtration, extraction, washing, drying, concentration, crystallization, chromatography, and the like. The intermediate products may be subjected to subsequent reactions without being purified.

Compounds (II) may embrace isomers, such as regioisomers, geometrical isomers and optical isomers. Mixtures of any possible isomers at any mixing ratio are included under the scope of the present invention.

Where a salt of Compound (II) is desired, a salt of Compound (II) as produced is purified, or a free compound as obtained is dissolved or suspended in an appropriate solvent, and an acid is added thereto to form a salt.

Compounds (II) or pharmaceutically acceptable salts thereof may exist in the form of an adduct with water or various solvents. These adducts are also included under the scope of the present invention.

Specific examples of Compounds (I) and (II) are shown in Table 1 below. In the Table, compounds marked with an asterisk are mixtures of regioisomers assigned to $R^2$ and $R^3$, but the ratios shown in the footnote correspond to the positions of $R^2/R^3$ or the positions of $R^3/R^2$.

TABLE 1

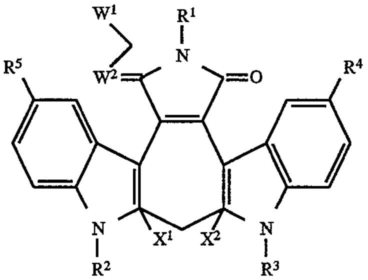

| Compd. | $W^1$, $W^2$ | $R^1$ | $R^2$ | $R^3$ | $R^4$ | $R^5$ | $X^1$, $X^2$ |
|---|---|---|---|---|---|---|---|
| 1 | H,H | THP | Me | Me | H | H | bond |
| 2* | H,H | THP | allyl | H | H | H | bond |
| 3 | H,H | THP | allyl | allyl | H | H | bond |
| 4 | H,H | THP | Hex | Hex | H | H | bond |
| 5 | H,H | THP | Bn | Bn | H | H | bond |
| 6 | H,H | THP | Pr | Pr | H | H | bond |
| 7* | H,H | THP | iPr | H | H | H | bond |
| 8 | H,H | THP | 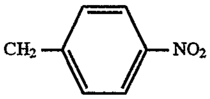 | 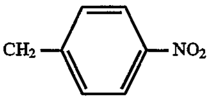 | H | H | bond |
| 9 | H,H | Me | Me | Me | H | H | bond |
| 10 | H,H | Bn | Me | Me | H | H | bond |
| 11 | H,H | Me | Bn | Bn | H | H | bond |
| 12 | H,H | Me | 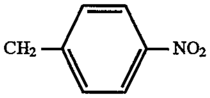 | 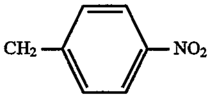 | H | H | bond |
| 13 | H,H | Me | 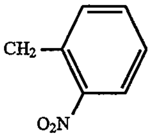 | 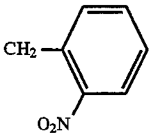 | H | H | bond |
| 14* | H,H | Me | 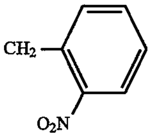 | H | H | H | bond |
| 15* | H,H | Me | 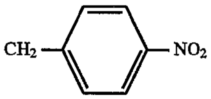 | H | H | H | bond |

*Mixture of regioisomers: 2 (1.4:1), 7 (7:1), 14 (4:1), 15 (12:1)

| Compd. | $W^1$, $W^2$ | $R^1$ | $R^2$ | $R^3$ | $R^4$ | $R^5$ | $X^1$, $X^2$ | Salt |
|---|---|---|---|---|---|---|---|---|
| 16 | $H_2$ | THP | 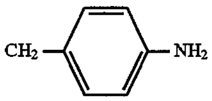 | 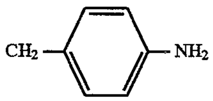 | H | H | bond | |
| 17 | H,H | Me | 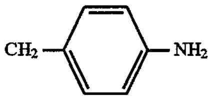 | 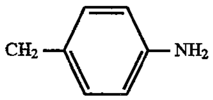 | H | H | bond | |
| 18* | H,H | Me | 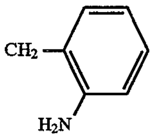 | H | H | H | bond | |

TABLE 1-continued

| | | | | | | | | |
|---|---|---|---|---|---|---|---|---|
| 19* | H,H | Me | 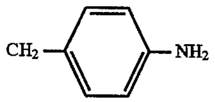 | H | H | H | bond | |
| 20 | H,H | Me | 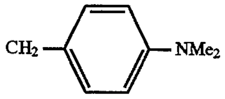 | 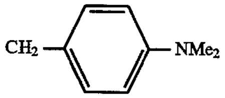 | H | H | bond | |
| 21* | H,H | Me | 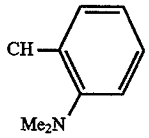 | H | H | H | bond | |
| 22 | O | Me | allyl | Me | H | H | bond | |
| 23 | O | Me | $(CH_2)_3OH$ | Me | H | H | bond | |
| 24 | O | Me | $(CH_2)_3Br$ | Me | H | H | bond | |
| 25 | O | Me | $(CH_2)_3NMe_2$ | Me | H | H | bond | HCl |
| 26 | O | Me | $(CH_2)NHMe$ | Me | H | H | bond | HCl |
| 27 | O | Me | $(CH_2)_3NEt_2$ | Me | H | H | bond | HCl |
| 28 | O | Me | 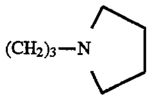 | Me | H | H | bond | HCl |
| 29 | O | Me | 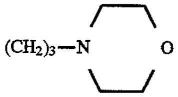 | Me | H | H | bond | HCl |

*Mixture of regioisomers: 18 (2.5:1), 19 (2.5:1), 21 (2.5:1)

| Compd. | $W^1$, $W^2$ | $R^1$ | $R^2$ | $R^3$ | $R^4$ | $R^5$ | X | Salt |
|---|---|---|---|---|---|---|---|---|
| 30 | O | Me | 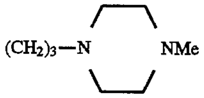 | Me | H | H | bond | 2HCl |
| 31 | O | Me | $(CH_2)_3NMePr$ | Me | H | H | bond | HCl |
| 32 | O | Me | 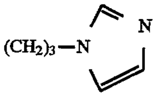 | Me | H | H | bond | HCl |
| 33 | O | Me | $(CH_2)_3N_3$ | Me | H | H | bond | |
| 34 | O | Me | $(CH_2)_3NH_2$ | Me | H | H | bond | |
| 35 | O | Me | $(CH_2)_3NH(C{=}NH)NH_2$ | Me | H | H | bond | |
| 36 | O | Me | $CH_2CH(OH)CH_2OH$ | Me | H | H | bond | |
| 37 | O | Me | $CH_2CH(OCHO)CH_2Br$ | Me | H | H | bond | |
| 38 | O | Me | $CH_2CH(OH)CH_2NMe_2$ | Me | H | H | bond | HCl |
| 39 | O | Me | $(CH_2)_3Br$ | Me | CHO | CHO | bond | |
| 40 | O | Me | $(CH_2)_3NMe_2$ | Me | OH | OH | bond | HCl |
| 41* | H,H | THP | allyl | H | H | H | bond | |
| 42 | H,H | THP | allyl | H | H | H | bond | |
| 43* | H,H | Me | allyl | Me | H | H | bond | |
| 44 | H,H | Me | $CH_2CH(OH)CH_3$ | Me | H | H | bond | |
| 45* | H,H | Me | $(CH_2)_3OH$ | Me | H | H | bond | |
| 46* | H,H | Me | $(CH_2)_3Br$ | Me | H | H | bond | |
| 47* | H,H | Me | $(CH_2)_3NMe_2$ | Me | H | H | bond | HCl |

*Mixture of regioisomers: 41 (4:1), 43 (4:1), 45 (4:1), 46 (4:1), 47 (5:1)

| Compd. | $W^1$, $W^2$ | $R^1$ | $R^2$ | $R^3$ | $R^4$ | $R^5$ | $X^1$, $X^2$ | Salt |
|---|---|---|---|---|---|---|---|---|
| 48 | H,H | Me | 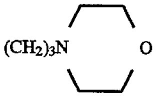 | Me | H | H | bond | HCl |
| 49 | H,H | Me | $(CH_2)_3N_3$ | Me | H | H | bond | |
| 50 | H,H | Me | $(CH_2)_3NH_2$ | Me | H | H | bond | HCl |
| 51 | H,H | Me | $(CH_2)_3NPr_2$ | Me | H | H | bond | HCl |
| 52 | H,H | Me | allyl | allyl | H | H | bond | |

TABLE 1-continued

| | | | | | | | | |
|---|---|---|---|---|---|---|---|---|
| 53* | H,H | Me | $CH_2CH(OH)Me$ | H | H | H | bond | HCl |
| 54 | H,H | Me | $(CH_2)_3OH$ | $(CH_2)_3OH$ | H | H | bond | |
| 55 | H,H | Me | $(CH_2)_3Br$ | $(CH_2)_3Br$ | H | H | bond | |
| 56 | H,H | Me | $(CH_2)_3NMe_2$ | $(CH_2)_3NMe_2$ | H | H | bond | 2HCl |
| 57 | H,H | Me | 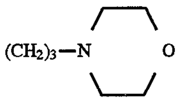 | 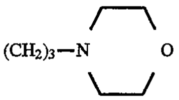 | H | H | bond | 2HCl |
| 58 | H,H | Me | $(CH_2)_3N_3$ | $(CH_2)_3N_3$ | H | H | bond | |
| 59 | H,H | Me | $(CH_2)_3NH_2$ | $(CH_2)_3NH_2$ | H | H | bond | |
| 60 | H,H | THP | $(CH_2)_3OH$ | $(CH_2)_3OH$ | H | H | bond | |
| 61 | H,H | $(CH_2)_5OH$ | $(CH_2)_3OH$ | $(CH_2)_3OH$ | H | H | bond | |
| 62* | H,H | $(CH_2)_5OH$ | $CH_2CH(OH)CH_3$ | H | H | H | bond | |
| 63* | H,H | THP | $(CH_2)_3OH$ | H | H | H | bond | |
| 64* | H,H | THP | $(CH_2)_3Br$ | H | H | H | bond | |
| 65* | H,H | THP | $(CH_2)_3NMe_2$ | H | H | H | bond | HCl |

*Mixture of regioisomers: 53 (1.5:1), 62 (2:1), 63 (1:1.5), 64 (1:1.5), 65 (1:1.5)

| Compd. | $W^1$, $W^2$ | $R^1$ | $R^2$ | $R^3$ | $R^4$ | $R^5$ | X | Salt |
|---|---|---|---|---|---|---|---|---|
| 66 | H,H | THP | $CH_2CO_2Et$ | $CH_2CO_2Et$ | H | H | bond | |
| 67* | H,H | THP | $CH_2CO_2Et$ | H | H | H | bond | |
| 68* | H,H | THP | $(CH_2)_2OH$ | H | H | H | bond | |
| 69* | H,H | THP | $(CH_2)_2NH_2$ | H | H | H | bond | |
| 70* | H,H | Me | $CH_2CO_2Et$ | H | H | H | bond | |
| 71* | H,H | Me | $(CH_2)_2OH$ | H | H | H | bond | |
| 72* | H,H | Me | $(CH_2)_2Br$ | H | H | H | bond | |
| 73* | H,H | Me | $(CH_2)_2NMe_2$ | H | H | H | bond | HCl |
| 74 | H,H | THP | $CH_2CO_2H$ | $CH_2CO_2H$ | H | H | bond | 2K |
| 75* | H,H | THP | $CH_2CO_2H$ | H | H | H | bond | K |
| 76 | O | Me | $(CH_2)_3NMe_2$ | Me | H | H | H,H | HCl |
| 77 | O | Me | Bn | Bn | H | H | H,H | |
| 78 | O | Me | 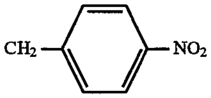 | 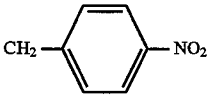 | H | H | H,H | |
| 79 | O | Me | 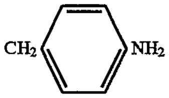 | 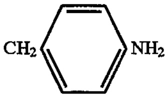 | H | H | H, H | 2HCl |

Mixture of regioisomers: 67 (2.5:1), 68 (2.5:1), 69 (2:1), 70 (4:1), 71 (4:1), 72 (4:1), 73 (4:1), 75(1.5:1)

| Compd. | $W^1$, $W^2$ | $R^1$ | $R^2$ | $R^3$ | $R^4$ | $R^5$ | $X^1$, $X^2$ | Salt |
|---|---|---|---|---|---|---|---|---|
| 80 | H,H | Me | H | H | H | H | bond | |
| 81 | O | Me | allyl | H | H | H | bond | |
| 82 | O | Me | allyl | allyl | H | H | bond | |
| 83 | O | Me | $CH_2CH(OH)CH_2OH$ | H | H | H | bond | |
| 84 | O | Me | $CH_2CH(OH)CH_2OH$ | $CH_2CH(OH)CH_2OH$ | H | H | bond | |
| 85 | H,H | H | $CH_2CO_2Et$ | $CH_2CO_2Et$ | H | H | bond | |
| 86 | H,H | H | $(CH_2)_3OH$ | $(CH_2)_3OH$ | H | H | bond | |
| 87* | H,H | H | $(CH_2)_2OH$ | H | H | H | bond | |
| 88 | H,H | H | 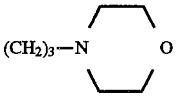 | H | H | H | bond | HCl |
| 89 | H,H | THP | H | H | H | H | bond | |
| 90 | H,H | H | Bn | Bn | H | H | bond | |
| 91 | H,H | H | Me | Me | H | H | bond | |
| 92* | H,H | H | $(CH_2)_3NMe_2$ | H | H | H | bond | HCl |
| 93 | O | Me | H | H | H | H | H,H | |
| 94 | O | Me | $(CH_2)_3NHi\text{-}Pr$ | Me | H | H | bond | HCl |
| 95 | O | Me | $(CH_2)_3NMei\text{-}Pr$ | Me | H | H | bond | HCl |
| 96 | O | Me | 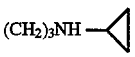 | Me | H | H | bond | HCl |
| 97 | O | Me | 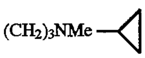 | Me | H | H | bond | HCl |

TABLE 1-continued

| | | | | | | | | |
|---|---|---|---|---|---|---|---|---|
| 98 | O | Me | 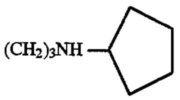 | Me | H | H | bond | HCl |
| 99 | O | Me | 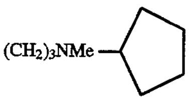 | Me | H | H | bond | HCl |
| 100 | O | Me | $(CH_2)_3NMe(CH_2)_3CH_3$ | Me | H | H | bond | HCl |
| 101 | O | Me | $(CH_2)_3NMeCH_2CHMe_2$ | Me | H | H | bond | HCl |
| 102 | O | Me | $(CH_2)_3NMe(CH_2)_2CHMe_2$ | Me | H | H | bond | HCl |
| 103 | O | Me | $(CH_2)_3NMeCHEt_2$ | Me | H | H | bond | HCl |
| 104 | O | Me | $(CH_2)_3NEtPr$ | Me | H | H | bond | HCl |
| 105 | O | Me | $(CH_2)_3NEti\text{-}Pr$ | Me | H | H | bond | HCl |
| 106 | O | Me | $(CH_2)_3NMe(CH_2)_2OH$ | Me | H | H | bond | HCl |
| 107 | O | Me | 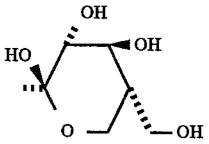 | H | H | H | bond | |
| 108 | O | Me | $(CH_2)_3NEt_2$ | Me | OH | OH | bond | HCl |
| 109 | O | Me | $(CH_2)_3Br$ | Me | Br | Br | bond | |
| 110 | O | Me | $(CH_2)_3NEt_2$ | Me | Br | Br | bond | HCl |

*Mixture of regioisomers: 87 (3:1), 92 (1:1.5)

Preparation of Compounds 80 to 84, which are disclosed in PCT/JP93/01346 (WO 94/06799), is shown in Reference Examples. Compounds 85 to 88, which are shown in Reference Examples, can be prepared according to the method similar to that described in Japanese Published Unexamined Patent Application No. 149520/90.

Physical properties of known Compounds 89 to 93 are shown be low.

Compound 89: Fab-MS (m/z): 396 $(M+1)^+$

Compound 90: Fab-MS (m/z): 492 $(M+1)^+$

Compound 91: Fab-MS (m/z): 339 $(M)^+$

Compound 92: Fab-MS (m/z): 397 $(M+1)^+$

Compound 93: Fab-MS (m/z): 342 $(M+1)^+$

Processes of preparation and more detailed physical properties of Compound 89 are described in *J. Chem. Soc. Perkin Trans I*, 2475 (1990); those of Compound 91 in *Bioorganic & Medicinal Chemistry Letters*, 3, 1959 (1993); those of Compound 93 in *Tetrahedron*, 44, 2887 (1988), respectively.

Compound (I) and pharmaceutically acceptable salts thereof can be used as such or in the form of various pharmaceutical compositions according to their pharmacological activity and the intended administration purpose. The pharmaceutical compositions according to the present invention can be prepared by uniformly mixing an effective amount of Compound (I) or a pharmaceutically acceptable salt thereof as an active ingredient with pharmaceutically acceptable carriers. The carriers may have a wide range form depending on the type of the preparation desired for the administration. The pharmaceutical compositions are preferably formulated into a unit dose form which is suited to oral or non-oral administration. The dose forms for non-oral administration include ointments and injections.

Tablets can be prepared using, in a conventional manner, excipients such as lactose, glucose, sucrose, mannitol, and methyl cellulose; disintegrating agents such as starch, sodium alginate, calcium carboxymethyl cellulose, and crystalline cellulose; lubricants such as magnesium stearate and talc; binders such as gelatin, polyvinyl alcohol, polyvinylpyrrolidone, hydroxypropyl cellulose, and methyl cellulose; surface active agents such as sucrose fatty acid esters and sorbitol fatty acid esters; and the like. Tablets each containing 50 to 200 mg of an active ingredient are appropriate.

Granules can be prepared using, in a conventional manner, excipients such as lactose and sucrose; disintegrating agents such as starch; binders such as gelatin; and the like. Powders are prepared using excipients such as lactose and mannitol, and the like in a conventional manner. Capsules are prepared using, in a conventional manner, gelatin, water, sucrose, gum arabic, sorbitol, glycerin, crystalline cellulose, magnesium stearate, talc, etc. Capsules each containing 50 to 200 mg of an active ingredient are appropriate. Syrups are prepared using saccharides such as sucrose, water, ethanol, etc. in a conventional manner.

For the preparation of ointments, ointment bases such as vaseline, liquid paraffin, lanolin, and macrogol, and emulsifying agents such as sodium lauryl lactate, benzalkonium chloride, sorbitan monofatty acid esters, sodium carboxymethyl cellulose, and gum arabic, and the like may be used in a conventional manner.

Injectable preparations can be prepared using, in a conventional manner, solvents such as water, physiological saline, vegetable oil (e.g., olive oil and peanut oil), ethyl oleate, and propylene glycol; solubilizing agents such as sodium benzoate, sodium salicylate, and urethane; isotonizing agents such as sodium chloride and glucose; preservatives such as phenol, cresol, p-hydroxybenzoic esters, and chlorobutanol; antioxidants such as ascorbic acid and sodium pyrosulfite; and the like.

Compound (I) and pharmaceutically acceptable salts thereof may be administered orally or non-orally as an ointment or an injection. The effective dose and the administration schedule vary depending on the administration route, the age, body weight and symptoms of the patient, and the like, but generally ranges 6.0 to 300 mg/kg/day in a single to 4 divided doses.

The toxicity and pharmacological activity of Compound (I) will be described by way of Test Examples.

Test Example 1

Megakaryocyte colony formation-stimulating activity

An eight-weeks-old BALB/c mouse was killed. Its femurs and cervical vertebrae were taken out, and both end sections thereof were cut off. Bone marrow cells were collected from the pieces cut off from the femurs and cervical vertebrae using a syringe containing IMDM (430-2200EA prepared by Gibco Co.), and then blown into a test tube. The test tube was allowed to stand for 5 minutes, and the supernatant was collected with a pipet. To a reaction mixture comprising the bone marrow cells (50,000 cells), bovine serum albumin (2%: A4508 made by Sigma Co.), transferrin (600 μg/ml: 652202 made by Boehringer Mannheim Co.), IL-3 (100 U/ml), cholesterol (16 μg/ml: 036-0641 made by Wako Co.) and agar (0.6%: 0142-02 made by Difco Laboratories) were separately added the test compounds at various concentrations, and 1 ml each of the mixtures was put into a 35-mm dish (Lux Co.), followed by incubation under the conditions of 37° C., 5% $CO_2$ and a humidity of 95% or more for 7 days. Separately, IL-3 alone was added to the bone marrow cells to prepare a control. After the incubation was completed, the agar was dried over a filter paper (1001-055 made by Whatman Co.) and then fixed with 2.5% glutaraldehyde, followed by acetylcholinesterase staining (ACHE staining).

The ACHE staining was carried out by the method described below.

ACHE staining: To each sample was added a solution comprising 0.67 mg/ml acetylthiocholine iodide, 2.94 mg/ml sodium citrate, 7.5 mg/ml copper (II) sulfate and 1.65 mg/ml potassium ferricyanide, and the mixture was allowed to stand at room temperature in the dark for 4–6 hours.

A group of 4 or more megakaryocytes which were stained reddish brown was regarded as a colony, and the number of colonies per dish was calculated using a microscope. The results are shown in Table 2 as relative values to the control.

(The table shows the relative values calculated on the basis of the control defined as 100.)

TABLE 2

| Compd. | Concn. (nM) | Rel. Value |
|---|---|---|
| Control | — | 100 |
| 9 | 1 | 128 |
| 20 | 1 | 140 |
| 26 | 1 | 117 |
| 53 | 1 | 107 |
| 80 | 1 | 111 |
| 81 | 10 | 113 |
| 82 | 1 | 101 |
| 83 | 1 | 111 |
| 84 | 10 | 132 |
| 85 | 1 | 125 |
| 86 | 1 | 131 |
| 87 | 1 | 108 |
| 88 | 1 | 120 |
| 89 | 1 | 110 |
| 90 | 10 | 106 |
| 91 | 1 | 111 |
| 92 | 1 | 128 |
| 93 | 1 | 109 |
| 110 | 1 | 137 |

TEST EXAMPLE 2

Platelet Production-Stimulating Activity in Mice

A test compound was intraperitoneally administered to four 7-week-old male BALB/c mice per group once a day for consecutive 5 days (day 1 to day 5). A control group (4 mice per group) received only the solvent (5% Tween 80/water). The blood was collected from the fundus oculi vein of each animal on the 15th day from the start of administration (day 15), and the number of the platelets was counted with a microcell counter (Model CC-180A, manufactured by Toa Iryo Denshi Co.). The rate of increase of the number of platelets in the test group (average) over the control (average) was calculated according to the following formula to evaluate the effect of the test compound. The results obtained are shown in Table 3.

Rate of Increase=A/B×100

A: the number of platelets in test group

B: the number of platelets in control group

TABLE 3

| Test Compd. | Dose (mg/kg) | Rate of increase (%) |
|---|---|---|
| 25 | 20 | 151 |
| 27 | 40 | 187 |
| 31 | 40 | 161 |
| 47 | 10 | 116 |
| 108 | 25 | 179 |
| 110 | 40 | 184 |

TEST EXAMPLE 3

Acute Toxicity

A solution (0.2 ml) of a test compound in phosphate-buffered physiological saline was intraperitoneally administered to a 6-week-old male DDY mice (3 mice per group). The 50% lethal dose ($LD_{50}$) was calculated from the survival rate after 24 hours from the administration. As a result, all the Compounds 1 to 110 tested had an LD50 of not less than 10 mg/kg.

The present invention will now be illustrated in detail with reference to Examples and Reference Examples, but it should be understood that the present invention is not construed as being limited thereto. In Examples, "brine", $MgSO_4$, AcOEt, $CHCl_3$, and MeOH stand for a saturated aqueous solution of sodium chloride, magnesium sulfate, ethyl acetate, chloroform, and methanol, respectively. Compounds (C) to (F) which are used as starting compounds are known compounds. Chemical structures of these compounds together with their reference literature are shown below.

Compound (C):

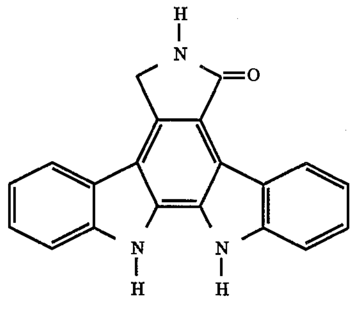

-continued

J. Antibiot., 39, 1072 (1986)

Compound (D):

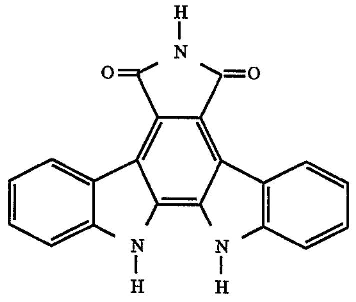

Pure Appl. Chem., 61, 281 (1989)

Compound (E):

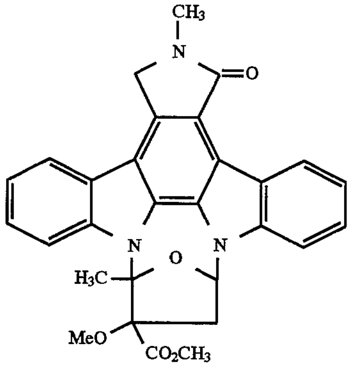

Japanese Published Unexamined Patent Application No. 295588/88

Compound (F):

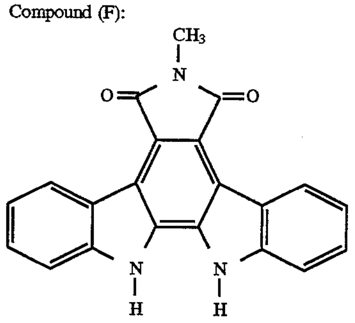

Tetrahedron Lett., 34, 5329 (1993)

EXAMPLE 1

Synthesis of Compound 1

In 6 ml of DMF was dissolved 100 mg (0.25 mmol) of known Compound 89, and 30 mg (0.75 mmol) of 60% sodium hydride was added thereto under cooling with ice, followed by stirring for 10 minutes. To the mixture was further added 0.047 ml (0.75 mmol) of methyl iodide at that temperature, followed by stirring for 2 hours. The reaction mixture was diluted with chloroform, and water added. The organic layer was separated, washed with brine, and dried over $MgSO_4$. The solvent was removed by evaporation, and the residue was purified by silica gel column chromatography (AcOEt/toluene=1/9) to give 81 mg (77%) of Compound 1.

$^1$HNMR (DMSO-$d_6$) δ: 1.557–2.138 (m, 6H), 3.625–3.677 (m, 1H), 4.001 (m, 1H), 4.266 (s, 3H), 4.308 (s, 3H), 5.050 (d, 1H, J=17.3 Hz), 5.138 (d, 1H, J=17.3 Hz), 5.453 (dd, 1H, J=2.0 Hz, 11.1 Hz), 7.291–7.801 (m, 6H), 8.172 (d, 1H, J=7.6 Hz), 9.390 (d, 1H, J=7.7 Hz).

Fab-MS (m/z): 436$(M+1)^+$

EXAMPLE 2

Synthesis of Compounds 2 and 3

In the same manner as in Example 1, 109 mg (30%) of Compound 2 (monoallyl compound) and 217 mg (54%) of Compound 3 (diallyl compound) were obtained from 337 mg (0.85 mmol) of Compound 89, 41 mg (1.02 mmol) of sodium hydride, and 0.088 ml (1.02 mmol) of allyl bromide.

Compound 2 (1.4:1 mixture of regioisomers):

$^1$HNMR (DMSO-$d_6$) δ: 1.562–2.149 (m, 6H), 3.628–3.719 (m, 1H), 3.991–4.022 (m, 1H), 4.679 (dd, 0.59H, J=1.3 Hz, 17.3 Hz), 4.757 (d, 0.41H, J=17.0 Hz), 5.003–5.172 (m, 3H), 5.465 (dd, 1H, J=1.7 Hz, 10.9 Hz), 5.576 (m, 2H), 6.111–6.222 (m, 1H), 7.173–8.177 (m, 7H), 9.302 (d, 0.41H, J=8.1 Hz), 9.353 (d, 0.59H, J=8.1 Hz), 11.555 (s, 0.41H), 11.713 (s, 0.59H).

Fab-MS (m/z): 436$(M+1)^+$

Compound 3:

$^1$HNMR (DMSO-$d_6$) δ: 1.563–2.154 (m, 6H), 3.657 (m, 1H), 4.008 (m, 1H), 5.044–5.478 (m, 11H), 6.153 (m, 2H), 7.240–7.640 (m, 6H), 8.167 (d, 1H, J=7.8 Hz), 9.415 (d, 1H, J=7.8 Hz).

Fab-MS (m/z): 476$(M+1)^+$

EXAMPLE 3

Synthesis of Compound 4

In the same manner as in Example 1, 31 mg (22%) of Compound 4 was obtained from 100 mg (0.25. mmol) of Compound 89, 30 mg (0.75 mmol) of sodium hydride, and 0.11 ml (0.75 mol) of hexyl iodide.

$^1$HNMR (DMSO-$d_6$) δ: 0.589 (t, 3H, J=7.2 Hz), 0.597 (t, 3H, J=7.2 Hz), 0.782–1.051 (m, 12H), 1.415–2.128 (m, 10H), 3.651 (m, 1H), 3.998 (m, 1H), 4.67 6 (t, 2H, J=7.3 Hz), 4.724 (t, 2H, J=7.3 Hz), 5.040 (d, 1H, J=17.5 Hz), 5.140 (d, 1H, J=17.5 Hz), 7.283–7.876 (m, 6H), 8.154 (d, 1H, J=7.7 Hz), 9.370 (d, 1H, J=7.4 Hz).

Fab-MS (m/z): 563$(M)^+$

EXAMPLE 4

Synthesis of Compound 5

In the same manner as in Example 1, 82 mg (47%) of Compound 5 was obtained from 119 mg (0.3 mmol) of Compound 89, 36 mg (0.9 mmol) of sodium hydride, and 0.1 ml (0.9 mmol) of benzyl bromide.

$^1$HNMR ($CDCl_3$) δ: 1.54–2.075 (m, 6H), 3.837 (m, 1H), 4.129 (m, 1H), 5.055 (d, 1H, J=16.6 Hz), 5.232 (d, 1H, J=16.6 Hz), 5.356 (s, 3H), 5.420 (s, 3H), 5.707 (d, 1H, J=8.0 Hz), 6.926–7.386 (m, 16H), 8.034 (dd, 1H, J=3.2 Hz, 5.8 Hz), 9.620 (dd, 1H, J=3.2 Hz, 5.8 Hz).

Fab-MS (m/z): 576$(M+1)^+$

EXAMPLE 5

Synthesis of Compound 6

In the same manner as in Example 1, 134 mg (56%) of Compound 6 was obtained from 200 mg (0.5 mmol) of Compound 89, 60 mg (1.5 mmol) of sodium hydride, and 0.15 ml (1.5 mmol) of propyl iodide.

$^1$HNMR ($CDCl_3$) δ: 0.539 (t, 3H, J=7.4 Hz), 0.579 (t, 3H, J=7.4 Hz), 1.532–2.173 (m, 6H), 3.807 (dt, 1H, J=2.7 Hz, 11.7 Hz), 4.111 (m, 1H), 4.551 (t, 2H, J=7.6 Hz), 4.614 (t, 2H, J=7.6 Hz), 4.989 (d, 1H, J=16.6 Hz), 5.155 (d, 1H, J=16.6 Hz), 5.665 (dd, 1H, J=2.4 Hz, 10.5 Hz), 7.333–7.643 (m, 6H), 7.992 (dd, 1H, J=0.9 Hz, 7.8 Hz), 9.538 (d, 1H, J=8.0 Hz).

Fab-MS (m/z): 479$(M)^+$

EXAMPLE 6

Synthesis of Compound 7

In the same manner as in Example 1, 13 mg (6%) of Compound 7 was obtained as a 7:1 mixture of regioisomers from 200 mg (0.5 mmol) of Compound 89, 60 mg (1.5 mmol) of sodium hydride, and 0.14 ml (1.5 mmol) of isopropyl bromide.

$^1$HNMR(DMSO-$d_6$) δ: 1.557–2.117 (m, 7.56H), 1.808 (d, 5.22H, J=6.9 Hz), 1.819 (d, 5.22H, J=6.9 Hz), 3.619–3.683 (m, 1H), 4.003 (m, 1H), 5.051 (d, 1H, J=17.3 Hz), 5.140 (d, 1H, J=17.3 Hz), 5.454 (dd, 1H, J=2.0 Hz, 11.0 Hz), 5.722 (qui, 1H, J=6.9 Hz), 7.141–7.931 (m, 7H), 8.152 (d, 0.87H, J=7.8 Hz), 8.450 (d, 0.13H, J=7.8 Hz), 9.407 (d, 0.13H, J=7.1 Hz), 9.474 (dd, 0.87H, J=0.5 Hz, 8.1 Hz), 11.848 (s, 0.13H), 11.869 (s, 0.87H).

Fab-MS (m/z): 437$(M)^+$

EXAMPLE 7

Synthesis of Compound 8

In the same manner as in Example 1, 24 mg (36%) of Compound 8 was obtained from 40 mg (0.5 mmol) of Compound 89, 12 mg (0.3 mmol) of sodium hydride, and 86 mg (0.4 mmol) of p-nitrobenzyl bromide.

$^1$HNMR (DMSO-$d_6$) δ: 1.587–2.135 (m, 6H), 3.664 (m, 1H), 4.020 (m, 1H), 5.119 (d, 1H, J=17.8 Hz), 5.214 (d, 1H, J=17.9 Hz), 5.483 (d, 1H, J=8.8 Hz), 5.630 (s, 2H), 5.701 (s, 2H), 7.112–7.469 (m, 10H), 8.049 (d, 2H, J=8.8 Hz), 8.065 (d, 2H, J=8.8 Hz), 8.226 (d, 1H, J=6.8 Hz), 9.437 (d, 1H, J=7.4 Hz).

Fab-MS (m/z): 666(M+1)+

EXAMPLE 8

Synthesis of Compound 9

In the same manner as in Example 1, 37 mg (42%) of Compound 9 was obtained from 78 mg (0.25 mmol) of Compound (C), 50 mg (1.25 mmol) of sodium hydride, and 0.095 ml (1.5 mmol) of methyl iodide.

$^1$HNMR ($CDCl_3$) δ: 3.288 (s, 3H), 4.132 (s, 3H), 4.209 (s, 3H), 4.819 (s, 2H), 7.378–7.559 (m, 6H), 7.903 (d, 1H, J=7.5 Hz), 9.545 (d, 1H, J=8.1 Hz).

Fab-MS (m/z): 353(M)+

EXAMPLE 9

Synthesis of Compound 10

In the same manner as in Example 1, 20 mg (59%) of Compound 10 was obtained from 33 mg (0.08 mol) of known Compound 91, 5 mg (0.12 mmol) of sodium hydride, and 0.019 ml (0.16 mmol) of benzyl bromide.

$^1$HNMR (DMSO-$d_6$) δ: 3.275 (s, 3H), 4.261 (s, 3H), 4.293 (s, 3H), 4.915 (s, 2H), 4.994 (s, 2H), 7.271–7.798 (m, 11H), 8.004 (d, 1H, J=7.9 Hz), 9.455 (d, 1H, J=7.6 Hz).

Fab-MS (m/z): 429(M)+

EXAMPLE 10

Synthesis of Compound 11

In the same manner as in Example 1, 24 mg (47%) of Compound 11 was obtained from 49 mg (0.1 mmol) of known Compound 90, 5 mg (0.12 mmol) of sodium hydride, and 0.009 ml (0.15 mmol) of methyl iodide.

$^1$HNMR (DMSO-$d_6$) δ: 3.278 (s, 3H), 5.108 (s, 2H), 5.598 (s, 2H), 5.657 (s, 2H), 6.854–7.458 (m, 16H), 8.071 (d, 1H, J=8.0 Hz), 9.465 (d, 1H, J=8.8 Hz).

Fab-MS (m/z): 506(M+1)+

EXAMPLE 11

Synthesis of Compound 12

In the same manner as in Example 1, 105 mg (59%) of Compound 12 was obtained from 100 mg (0.3 mmol) of Compound 80 described in Reference Example 1 hereinafter given, 36 mg (0.9 mmol) of sodium hydride, and 194 mg (0.9 mmol) of p-nitrobenzyl bromide.

$^1$HNMR ($CDCl_3$) δ: 3.287 (s, 3H), 5.111 (s, 2H), 5.590 (s, 2H), 5.657 (s, 2H), 7.130–7.457 (m, 10H), 8.067 (d, 2H, J=8.8 Hz), 8.077 (d, 2H, J=8.8 Hz), 8.103 (d, 1H, J=8.1 Hz), 9.491 (d, 1H, J=7.8 Hz).

Fab-MS (m/z): 596(M+1)+

EXAMPLE 12

Synthesis of Compound 13

In the same manner as in Example 1, 77 mg (43%) of Compound 13 was obtained from 100 mg (0.3 mmol) of Compound 80 described in Reference Example 1, 36 mg (0.9 mmol) of sodium hydride, and 194 mg (0.9 mmol) of o-nitrobenzyl bromide.

$^1$HNMR (DMSO-$d_6$) δ: 5.173 (s, 2H), 5.717 (s, 2H), 5.775 (s, 2H), 7.090–7.712 (m, 12H), 8.126–8.169 (m, 3H), 9.577 (d, 1H, J=6.8 Hz).

Fab-MS (m/z): 596(M+1)+

EXAMPLE 13

Synthesis of Compound 14

In the same manner as in Example 1, 40 mg (29%) of Compound 14 was obtained as a 4:1 mixture of regioisomers from 100 mg (0.3 mmol) of Compound 80 described in Reference Example 1, 12 mg (0.3 mmol) of sodium hydride, and 65 mg (0.3 mmol) of o-nitrobenzyl bromide.

$^1$HNMR (DMSO-$d_6$) δ: 5.091 (s, 0.4H), 5.132 (s, 1.6H), 6.116 (d, 0.2H, J=8.1 Hz), 6.211 (d, 0.8H, J=7.1 Hz), 6.552 (s, 0.4H), 6.567 (s, 1.6H), 7.191–7.668 (m, 8H), 8.037 (d, 0.8H, J=7.6 Hz), 8.326 (dd, 1H, J=1.4 Hz, 8.3 Hz), 9.349 (d, 0.8H, J=7.9 Hz), 9.479 (d, 0.2H, J=8.3 Hz), 11.502 (s, 0.8H), 11.653 (s, 0.2H).

Fab-MS (m/z): 461(M+1)+

EXAMPLE 14

Synthesis of Compound 15

In the same manner as in Example 1, 131 mg (32%) of Compound 15 was obtained as a 12:1 mixture of regioisomers from 300 mg (0.9 mmol) of Compound 80 described in Reference Example 1, 36 mg (0.9 mmol) of sodium hydride, and 195 mg (0.9 mmol) of p-nitrobenzyl bromide.

$^1$HNMR (DMSO-$d_6$) δ: 5.082 (s, 0.16H), 5.099 (s, 1.84H), 6.365 (s, 0.16H), 6.383 (s, 1.84H), 7.218–7.717 (m, 8H), 8.087–8.122 (m, 3H), 9.355 (d, 0.92H, J=7.9 Hz), 9.434 (d, 0.08H, J=7.5 Hz), 11.650 (s, 0.92H), 11.795 (s, 0.08H).

Fab-MS (m/z): 460(M)+

EXAMPLE 15

Synthesis of Compound 16

In 20 ml of THF was dissolved 227 mg of Compound 8, and 50 mg of 10% palladium-on-carbon was added thereto, followed by stirring at room temperature in a hydrogen stream for 1 hour. The reaction mixture was filtered using Celite, the solvent was removed by evaporation, and the residue was purified by preparative TLC (10% MeOH/$CHCl_3$) to give 17 mg (8%) of Compound 16.

$^1$HNMR ($CDCl_3$) δ: 1.613–2.107 (m, 6H), 3.828 (dt, 1H, J=2.4 Hz, 11.8 Hz), 4.135 (m, 1H), 5.024 (d, 1H, J=16.4 Hz), 5.201 (d, 1H, J=16.4 Hz), 5.307 (s, 2H), 5.361 (s, 2H), 5.694 (dd, 1H, J=2.3 Hz, 10.5 Hz), 6.561–6.582 (m, 4H), 6.756 (d, 1H, J=8.4 Hz), 6.788 (d, 1H, J=8.3 Hz), 7.157–7.385 (m, 6H), 7.994 (dd, 1H, J=1.5 Hz, 6.3 Hz), 9.605 (dt, 1H, J=7.8 Hz, 1.2 Hz).

Fab-MS (m/z): 606(M+1)+

EXAMPLE 16

Synthesis of Compound 17

In 10 ml of THF was dissolved 50 mg of Compound 12, and 5 mg of $PtO_2$ was added thereto, followed by stirring at room temperature in a hydrogen stream for 40 minutes. The reaction mixture was filtered using Celite, the solvent was evaporated, the residue was dissolved in 5 ml of THF, 1 ml of 0.6N HCl/AcOEt added to the solution, and the precipitate thus formed was collected by filtration to afford 48 mg (93%) of Compound 17.

$^1$HNMR (DMSO-$d_6$) δ: 3.275 (s, 3H), 5.091 (s, 2H), 5.571 (s, 2H), 5.631 (s, 2H), 6.911–7.473 (m, 14H), 8.065 (d, 1H, J=7.5 Hz), 9.452 (d, 1H, J=8.0 Hz).

Fab-MS (m/z): 536(M+1)+

EXAMPLE 17

Synthesis of Compound 18

In the same manner as in Example 16, 21 mg (45%) of Compound 18 was obtained as a 2.5:1 mixture of regioisomers from 45 mg of Compound 14 and 5 mg of $PtO_2$.

$^1$HNMR (DMSO-$d_6$) δ: 5.080 (s, 0.56H), 5.103 (s, 1.44H), 6.009 (d, 0.28H, J=6.7 Hz), 6.035 (s, 2H), 6.094 (d, 0.72H, J=7.7 Hz), 7.142–7.707 (m, 6H), 8.046 (d, 0.28H, J=7.7 Hz), 8.095 (d, 0.72H, J=7.6 Hz), 9.341 (d, 0.72H, J=8.0 Hz), 9.423 (d, 0.28H, J=7.9 Hz), 11.701 (s, 0.72H), 11.848 (s, 0.28H).

Fab-MS (m/z): 430(M)+

EXAMPLE 18

Synthesis of Compound 19

In 3 ml of DMF was dissolved 121 mg of Compound 15, and 65 mg of 20% $Pd(OH)_2/C$ was added thereto, followed by stirring at room temperature in a hydrogen stream for 2.5 hours. The reaction mixture was filtered using Celite, the solvent was evaporated, and the residue was purified by silica gel column chromatography (10% acetone/toluene) to give 80 mg (72%) of Compound 19 as a 2.5:1 mixture of regioisomers.

$^1$HNMR (DMSO-$d_6$) δ: 5.060 (s, 1.44H), 5.067 (s, 0.56H), 5.967 (s, 0.56H), 5.984 (s, 1.44H), 6.370 (d, 0.56H, J=8.5 Hz), 6.384 (d, 1.44H, J=8.5 Hz), 6.853 (d, 0.56H, J=8.5 Hz), 6.901 (d, 1.44H, J=8.5 Hz), 7.216–7.752 (m, 6H), 8.036 (d, 0.72H, J=7.5 Hz), 9.359 (d, 0.28H, J=7.9 Hz), 9.382 (d, 0.72H, J=8.3 Hz), 11.679 (s, 0.72H), 11.816 (s, 0.28H).

Fab-MS (m/z): 431(M+1)+

EXAMPLE 19

Synthesis of Compound 20

In a mixed solvent of 0.2 ml of THF and 0.3 ml of MeOH was dissolved 8 mg (0.013 mmol) of Compound 17, and 0.046 ml of 35% formaldehyde and 8 mg of sodium cyanoborohydride were added to the solution while cooling with ice. After adjusting the pH to 3 to 4 with 3N HCl, the mixture was stirred for 4.5 hours. The reaction mixture was diluted with $CHCl_3$, washed with sodium hydrogencarbonate and then with brine, and dried over sodium sulfate. The solvent was evaporated, and the residue was purified by preparative TLC (2% MeOH/$CHCl_3$) to give 6 mg (75%) of Compound 20.

$^1$HNMR ($CDCl_3$) δ: 2.939 (s, 12H), 3.400 (s, 3H), 4.969 (s, 2H), 5.337 (s, 2H), 5.385 (s, 2H), 6.625 (d, 4H, J=8.5 Hz), 6.830 (d, 2H, J=8.8 Hz), 6.844 (d, 2H, J=8.8 Hz), 7.180–7.384 (m, 6H), 7.940 (d, 1H, J=7.7 Hz), 9.635 (d, 1H, J=7.3 Hz).

Fab-MS (m/z): 592(M+1)+

EXAMPLE 20

Synthesis of Compound 21

In the same manner as in Example 19, 5 mg (68%) of Compound 21 was obtained as a 2.5:1 mixture of regioisomers from 10 mg (0.016 mmol) of Compound 18.

$^1$HNMR ($CDCl_3$) δ: 2.995 (s, 6H), 3.101 (s, 2.16H), 3.135 (s, 0.84H), 4.084 (s, 2H), 5.541 (s, 2H), 6.634–7.638 (m, 10H), 7.711 (d, 1H, J=8.3 Hz), 9.533 (d, 0.72H, J=7.9 Hz), 9.653 (d, 0.28H, J=7.9 Hz), 9.744 (s, 0.72H), 10.361 (s, 0.28H).

Fab-MS (m/z): 459(M+1)+

EXAMPLE 21.

Synthesis of Compound 22

In 250 ml of DMF was dissolved 3.89 g (11.9 mmol) of Compound (C), and 3.30 g (23.9 mmol) of potassium carbonate was added thereto, followed by stirring at room temperature in an argon atmosphere for 2 hours. To the mixture was added 1.48 ml (23.8 mmol) of methyl iodide, and the stirring was continued for an additional period of 3.5 hours. The reaction mixture was poured into ice-water, followed by stirring for 1 hour. The precipitate thus formed was collected by filtration and dried under reduced pressure. The resulting crystals were dissolved in 300 ml of DMF, and 1.98 g (17.6 mmol) of potassium tert-butoxide was added thereto at 0° C., followed by stirring in an argon atmosphere for 1 hour. To the mixture was added 1.53 ml (17.7 mmol)

of allyl bromide, followed by further stirring at room temperature for 5 hours. The reaction was stopped by addition of ice-water, the reaction mixture was extracted with THF, the extract was washed with brine and dried over $MgSO_4$, and the solvent was evaporated. The residue was triturated with isopropyl alcohol to give 3.07 g (66%) of Compound 22.

$^1$HNMR (DMSO-$d_6$) δ: 3.006 (s, 3H), 4.060 (s, 3H), 5.151 (d, 2H, J=3.9 Hz), 5.246 (dd, 1H, J=1.2 Hz, 17.3 Hz), 5.360 (dd, 1H, J=1.2 Hz, 10.5 Hz), 6.177 (ddt, 1H, J=3.9 Hz, 10.5 Hz, 17.3 Hz), 7.35–7.43 (m, 2H), 7.56–7.71 (m, 4H), 9.052 (d, 1H, J=7.9 Hz), 9.102 (d, 1H, J=7.8 Hz).

Fab-MS (m/z): 394 (M+1)+

EXAMPLE 22

Synthesis of Compound 23

In 100 ml of THF was dissolved 996 mg (2.53 mmol) of Compound 22, and 3.09 g (25.3 mmol) of a 9-BBN dimer was added thereto, followed by stirring at room temperature overnight in an argon atmosphere. The reaction mixture was cooled to 0° C., and 9 ml of a 1N aqueous sodium hydroxide solution and 9 ml of 35% aqueous hydrogen peroxide were added thereto, followed by further stirring for 30 minutes. The reaction mixture was diluted with water and extracted with AcOEt. The extract was washed successively with water and brine and dried over $MgSO_4$, and the solvent was removed by evaporation. The residue was purified by silica gel column chromatography ($CHCl_3$/MeOH=40/1). Recrystallization from an AcOEt-diisopropyl ether mixed solvent gave 485 mg (47%) of Compound 23.

$^1$HNMR (DMSO-$d_6$) δ: 1.72–1.78 (m, 2H), 3.11–3.16 (m, 2H), 3.144 (s,3H), 4.227 (s, 3H), 4.451 (t, 1H, J=5.0 Hz), 4.846 (t, 2H, J=7.5 Hz), 7.38–7.44 (m, 2H), 7.629 (ddd, 1H, J=1.2 Hz, 7.0 Hz, 8.2 Hz), 7.653 (ddd, 1H, J=1.2 Hz, 7.1 Hz, 8.3 Hz), 7.766 (d, 1H, J=8.2 Hz), 7.861 (d, 1H, J=8.3 Hz), 9.129 (d, 1H, J=7.9 Hz), 9.157 (d, 1H, J=7.9 Hz).

Fab-MS (m/z): 412 $(M+1)^+$

EXAMPLE 23

Synthesis of Compound 24

In 5 ml of DMF was dissolved 376 mg (0.914 mmol) of Compound 23, and 721 mg (2.75 mmol) of triphenylphosphine and 0.14 ml (2.7 mmol) of bromine were added thereto at 0° C. in an argon atmosphere, followed by stirring at room temperature for hours. Water was added to stop the reaction, and the reaction mixture was extracted with AcOEt. The extract was washed successively with water and brine and dried over $MgSO_4$. The solvent was evaporated, and the residue was purified by silica gel column chromatography (AcOEt/toluene=1/15) to yield 372 mg (86%) of Compound 24.

$^1$HNMR (DMSO-$d_6$) δ: 2.00–2.07 (m, 2H), 3.124 (s, 3H), 3.151 (t, 2H, J=6.4 Hz), 4.231 (s, 3H), 4.925 (t, 2H, J=7.2 Hz), 7.40–7.45 (m, 2H), 7.62–7.68 (m, 2H), 7.765 (d, 1H, J=8.3 Hz), 7.872 (d, 1H, J=8.3 Hz), 9.106 (d, 1H, J=7.8 Hz), 9.135 (d, 1H, J=8.1 Hz).

Fab-MS (m/z): 474 $(M+1)^+$

EXAMPLE 24

Synthesis of Compound 25

In 25 ml of DMF was dissolved 180 mg (0.38 mmol) of Compound 24, and 0.14 ml (1.6 mmol) of a 50% aqueous solution of dimethylamine was added thereto, followed by stirring at room temperature for one day. Ice-water was added to the reaction mixture, and the formed precipitate was collected by filtration and dried under reduced pressure. The resulting crystals were dissolved in $CHCl_3$, and a 0.88N HCl (AcOEt solution) was added to the solution, followed by stirring at room temperature for 1 hour. The precipitate thus formed was collected by filtration, washed with AcOEt, and dried under reduced pressure to give 147 mg (81%) of Compound 25.

$^1$HNMR (DMSO-$d_6$) δ: 1.90–1.99 (m, 2H), 2.570 (s, 3H), 2.908 (t, 2H, J=7.7 Hz), 3.143 (s, 3H), 4.227 (s, 3H), 4.820 (t, 2H, J=7.9 Hz), 7.434 (ddd, 1H, J=0.9, 7.0, 7.9 Hz), 7.63–7.70 (m, 2H), 7.765 (d, 1H, J=8.3 Hz), 7.946 (d, 1H, J=8.3 Hz), 9.123 (d, 1H, J=7.9 Hz), 9.156 (d, 1H, J=7.9 Hz).

Fab-MS (m/z): 439 $(M+1)^+$

EXAMPLE 25

Synthesis of Compound 26

In the same manner as in Example 24, 47 mg (62%) of Compound 26 was obtained from 81 mg (0.170 mmol) of Compound 24, 0.14 ml (1.8 mmol) of a 40% aqueous methylamine solution, and 0.88N HCl (AcOEt solution).

$^1$HNMR (DMSO-$d_6$) δ: 1.80–1.87 (m, 2H), 2.362 (t, 2H, J=5.4 Hz), 2.505 (s, 3H), 3.171 (s, 3H), 4.240 (s, 3H), 4. 864 (t, 2H, J=7.6 Hz), 7.447 (t, 2H, J=7.3 Hz), 7.668 (ddd, 1H, J=1.1, 7.3, 8.4 Hz), 7.682 (ddd, 1H, J=1.1, 7.3, 8.4 Hz), 7.788 (d, 1H, J=8.4 Hz), 7.946 (d, 1H, J=8.4 Hz), 9.142 (dd, 1H, J=1.1, 7.3 Hz), 9.173 (d, 1H, J=7.3 Hz).

Fab-MS (m/z): 425 $(M+1)^+$

EXAMPLE 26

Synthesis of Compound 27

In the same manner as in Example 24, 58 mg (74%) of Compound 27 was obtained from 76 mg (0.16 mmol) of Compound 24, 0.17 ml (1.6 mmol) of diethylamine, and 0.88N HCl (AcOEt solution).

$^1$HNMR (DMSO-$d_6$) δ: 0.940 (t, 6H, J=7.3 Hz), 1.90–1.99 (m, 2H), 2.74–2.79 (m, 2H), 2.85–2.90 (m, 4H), 3.201 (s, 3H), 4.249 (s, 3H), 4.882 (t, 2H, J=7.3 Hz), 7.458 (ddd, 1H, J=1.0, 7.0, 8.0 Hz), 7.681 (ddd, 1H, J=1.2, 7.0, 8.2 Hz), 7.689 (ddd, 1H, J=1.2, 7.0, 8.2 Hz), 7.810 (d, 1H, J=8.2 Hz), 7.970 (d, 1H, J=8.2 Hz), 9.151 (dd, 1H, J=1.2, 7.8 Hz), 9.189 (dd, 1H, J=1.2, 8.0 Hz).

Fab-MS (m/z): 467 $(M+1)^+$

EXAMPLE 27

Synthesis of Compound 28

In the same manner as in Example 24, 54 mg (67%) of Compound 28 was obtained from 74 mg (0.16 mmol) of Compound 24, 0.13 ml (1.6 mmol) of pyrrolidine, and 0.88N HCl (AcOEt solution).

$^1$HNMR (DMSO-$d_6$) δ: 1.71–1.74 (m, 2H), 1.85–1.93 (m, 4H), 2.76–2.80 (m, 2H), 2.93–2.98 (m, 2H), 3.190 (s, 3H), 4.241 (s, 3H), 4.859 (t, 2H, J=7.6 Hz), 7.44–7.48 (m, 2H), 7.66–7.71 (m, 2H), 7.802 (d, 1H, J=8.2 Hz), 7.958 (d, 1H, J=8.3 Hz), 9.152 (dd, 1H, J=0.5, 7.9 Hz), 9.188 (dd, 1H, J=0.5, 7.9 Hz).

Fab-MS (m/z): 465 $(M+1)^+$

EXAMPLE 28

Synthesis of Compound 29

In 25 ml of DMF was dissolved 180 mg (0.38 mmol) of Compound 24, and 0.066 ml (0.76 mmol) of morpholine was added thereto, followed by stirring at 80° C. for 3 hours in an argon atmosphere. After cooling to room temperature, ice-water was added to the reaction mixture, and the precipitate thus formed was collected by filtration and dried under reduced pressure. The crude product was purified by silica gel chromatography ($CHCl_3$/MeOH=50/1). The purified product was dissolved in AcOEt, and 0.88N HCl (AcOEt solution) was added thereto, followed by stirring at room temperature for 1 hour. The thus formed precipitate was collected by filtration, washed with AcOEt, and dried under reduced pressure to give 138 mg (70%) of Compound 29.

$^1$HNMR (DMSO-$d_6$) δ: 1.9–2.1 (br, 2H), 2.8–2.9 (br, 2H), 2.9–3.0 (br, 2H), 3.173 (s, 3H), 3.2–3.3 (br, 2H), 3.5–3.7 (br, 2H), 3.8–3.9 (br, 2H), 4.226 (s, 3H), 4. 810 (t, 2H, J=7.7 Hz), 7.436 (ddd, 1H, J=0.9 Hz, 7.1, 8.0 Hz), 7.659 (ddd, 1H, J=1.2, 7.1, 8.3 Hz), 7.673 (ddd, 1H, J=1.2, 7.1, 8.3 Hz), 7.767 (d, 1H, J=8.3 Hz), 7.941 (d, 1H, J=8.3 Hz), 9.117 (dd, 1H, J=1.2, 8.0 Hz), 9.149 (dd, 1H, J=1.2, 8.0 Hz).

Fab-MS (m/z): 481 $(M+1)^+$

EXAMPLE 29

Synthesis of Compound 30

In the same manner as in Example 28, 65 mg (67%) of Compound 30 was obtained from 84 mg (0.18 mmol) of Compound 24, 0.20 ml (1.6 mmol) of 1-methylpiperazine, and 0.88N HCl (AcOEt solution).

$^1$HNMR (DMSO-$d_6$) δ: 1.8–2.0 (br, 2H), 2.4–3.6 (br, 10H), 2.511 (s, 3H), 3.166 (s, 3H), 4.243 (s, 3H), 4.853 (t, 2H, J=7.2 Hz), 7.439 (t, 1H, J=7.3 Hz), 7.447 (ddd, 1H, J=0.8, 7.0, 7.8 Hz), 7.657 (ddd, 1H, J=1.0, 7.3, 8.3 Hz), 7.683 (ddd, 1H, J=1.1, 7.0, 8.1 Hz), 7.794 (d, 1H, J=8.3 Hz), 7.953 (d, 1H, J=8.1 Hz), 9.140 (d, 1H, J=7.3 Hz), 9.165 (d, 1H, J=7.8 Hz).

Fab-MS (m/z): 494 $(M+1)^+$

EXAMPLE 30

Synthesis of Compound 31

In a mixed solvent of 5 ml of THF and 5 ml of MeOH was dissolved 86 mg (0.18 mmol) of Compound 26, and 0.056 ml (0.78 mmol) of propanal and 48 mg (0.76 mmol) of sodium cyanoborohydride were added thereto. The mixture was stirred at room temperature overnight while adjusting the pH at 5 to 7 with 10% acetic acid (MeOH solution). The solvent was removed by evaporation under reduced pressure, and the residue was diluted with water and brine and extracted with THF. The extract was washed with brine and dried over $MgSO_4$. The solvent was evaporated, and the residue was purified by TLC ($CHCl_3$/MeOH/aqueous ammonia=200/9/1). The purified product was dissolved in $CHCl_3$, and 0.88N HCl (AcOEt solution) was added thereto, followed by stirring at room temperature for 1 hour. The precipitate was collected by filtration, washed with AcOEt, and dried under reduced pressure to afford 55 mg (71%) of Compound 31.

$^1$HNMR (DMSO-$d_6$) δ: 0.718 (t, 3H, J=7.4 Hz), 1.35–1.43 (m, 2H), 1.93–1.99 (m, 2H), 2.516 (s, 3H), 2.72–2.87 (m, 4H), 3.172 (s, 3H), 4.240 (s, 3H), 4.847 (t, 2H, J=7.7 Hz), 7.43–7.47 (m, 2H), 7.673 (ddd, 1H, J=1.2, 7.0, 8.2 Hz), 7.683 (ddd, 1H, J=1.2, 7.1, 8.3 Hz), 7.788 (d, 1H, J=8.2 Hz), 7.960 (d, 1H, J=8.3 Hz), 9.141 (dd, 1H, J=1.2, 7.8 Hz), 9.175 (dd, 1H, J=1.2, 7.9 Hz), 9.6–9.8 (br, 1H).

Fab-MS (m/z): 467 $(M+1)^+$

EXAMPLE 31

Synthesis of Compound 32

In 8 ml of DMF was dissolved in 50 mg (0.73 mmol) of imidazole, and 24 mg (0.60 mmol) of 60% sodium hydride was added to the solution at 0° C., followed by stirring for 10 minutes in an argon atmosphere. To the mixture was added 86 mg (0.18 mmol) of Compound 24, and the stirring was continued at room temperature for 20 minutes. The reaction was stopped by addition of water, and the reaction mixture was extracted with AcOEt. The extract was washed successively with water and brine and dried over $MgSO_4$. The solvent was evaporated, and the residue was purified by TLC ($CHCl_3$/MeOH/triethylamine=25/1/1). The purified product was dissolved in $CHCl_3$, and 0.88N HCl was added thereto, followed by stirring at room temperature for 1 hour. The precipitate was collected by filtration, washed with AcOEt, and dried under reduced pressure to yield 53 mg (62%) of Compound 32.

$^1$HNMR (DMSO-$d_6$) δ: 2.10–2.18 (m, 2H), 3.172 (s, 3H), 3.980 (t, 2H, J=7.0 Hz), 4.144 (s, 3H), 4.831 (t, 2H, J=7.4 Hz), 7.434 (d, 1H, J=1.7 Hz), 7.440 (ddd, 1H, J=0.7, 7.1, 7.8 Hz), 7.444 (ddd, 1H, J=0.9, 7.0, 7.9 Hz), 7.480 (t, 1H, J=1.7 Hz), 7.647 (ddd, 1H, J=1.1, 7.1, 8.2 Hz), 7.681 (ddd, 1H, J=1.2, 7.0, 8.2 Hz), 7.757 (d, 1H, J=8.2 Hz), 7.861 (d, 1H, J=8.2 Hz), 9.137 (d, 1H, J=7.8 Hz), 9.156 (d, 1H, J=7.9 Hz).

Fab-MS (m/z): 462 $(M+1)^+$

EXAMPLE 32

Synthesis of Compound 33

In 30 ml of DMF was dissolved 448 mg (0.95 mmol) of Compound 24, and 186 mg (2.86 mmol) of sodium azide was added thereto, followed by stirring in an argon atmosphere at 100° C. for 4 hours and then at room temperature overnight. The reaction was stopped by addition of water and brine, and the reaction mixture was extracted with THF. The extract was washed with brine and dried over $MgSO_4$. The solvent was evaporated, and the residue was purified by silica gel column chromatography (AcOEt/toluene=1/25) to give 348 mg (84%) of Compound 33.

$^1$HNMR ($CDCl_3$) δ: 1.73–1.80 (m, 2H), 2.861 (t, 2H, J=6.2 Hz.), 3.280 (s, 3H), 4.170 (s, 3H), 4.802 (t, 2H, J=7.1 Hz), 7.41–7.48 (m, 2H), 7.53–7.66 (m, 4H), 9.24–9.30 (m, 2H).

Fab-MS (m/z): 437 $(M+1)^+$

EXAMPLE 33

Synthesis of Compound 34

In 7 ml of DMF was dissolved 343 mg (0.79 mmol) of Compound 33, and 176 mg of 20% $Pd(OH)_2$-on-carbon was added thereto, followed by stirring at room temperature for 4.5 hours in a hydrogen atmosphere. The reaction mixture was filtered using Celite, and the solvent was evaporated. The residue was purified by silica gel column chromatography ($CHCl_3$/MeOH/aqueous ammonia=200/10/1). Recrystallization from isopropyl alcohol gave 162 mg (50%) of Compound 34.

$^1$HNMR ($CDCl_3$) δ: 1.65–1.73 (m, 2H), 2.242 (t, 2H, J=6.8 Hz), 3.299(s, 3H), 4.175 (s, 3H), 4.812 (t, 2H, J=7.1 Hz), 7.41–7.47 (m, 2H), 7.51–7.66 (m, 4H), 9.25–9.31 (m, 2H).

Fab-MS (m/z): 411 $(M+1)^+$

EXAMPLE 34

Synthesis of Compound 35

In a mixed solvent of 2 ml of DMF and 3 ml of ethanol was dissolved 84 mg (0.20 mmol) of Compound 34, and 17 mg (0.20 mmol) of sodium hydrogencarbonate and 62 mg (0.31 mmol) of 3,5-dimethylpyrazole-1-carboxyamidine nitrate were added thereto. The mixture was heated under reflux for 5 hours and then stirred at room temperature overnight. The solvent was evaporated under reduced pressure, and the residue was purified by TLC ($CHCl_3$/MeOH/aqueous ammonia=44/10/1) and triturated with 20% ethanol to give 49 mg (53%) of Compound 35.

$^1$HNMR (DMSO-$d_6$) δ: 1.73–1.78 (m, 2H), 2.78–2.83 (m, 2H), 3.178 (s, 3H), 4.226 (s, 3H), 4.825 (t, 2H, J=7.4 Hz), 6.6–7.2 (br, 3H), 7.352 (t, 1H, J=5.6 Hz), 7.442 (ddd, 1H, J=0.8, 7.1, 7.9 Hz), 7.447 (ddd, 1H, J=0.9, 7.1, 8.0 Hz), 7.662 (ddd, 1H, J=1.2, 7.1, 8.3 Hz), 7.681 (ddd, 1H, J=1.2, 7.1, 8.3 Hz), 7.779 (d, 1H, J=8.3 Hz), 7.881 (d, 1H, J=8.3 Hz), 9.145 (d, 1H, J=7.9 Hz), 9.177 (d, 1H, J=8.0 Hz).

Fab-MS (m/z): 453 $(M+1)^+$

EXAMPLE 35

Synthesis of Compound 36

In a mixed solvent of 20 ml of THF and 2 ml of pyridine was dissolved 464 mg (1.18 mmol) of Compound 22, and 30 mg (0.12 mmol) of osmium tetroxide and 557 mg (4.75 mmol) of N-methylmorpholine N-oxide were added thereto, followed by stirring at room temperature for one day. The reaction was ceased by addition of an aqueous sodium hydrogensulfite solution, and the reaction mixture was extracted with THF. The extract was washed successively with dilute hydrochloric acid and brine and dried over $MgSO_4$. The solvent was evaporated, and the residue was purified by silica gel column chromatography ($CHCl_3$/MeOH=50/1) to give 191 mg (38%) of Compound 36.

$^1$HNMR (DMSO-$d_6$) δ: 3.144 (t, 2H, J=5.4 Hz), 3.173 (s, 3H), 3.63–3.72 (m, 1H), 4.248 (s, 3H), 4.445 (d, 1H, J=5.6 Hz), 4.668 (t, 1H, J=5.4 Hz), 4.787 (dd, 1H, J=8.5, 14.9 Hz), 4.964 (dd, 1H, J=3.7, 14.9 Hz), 7.35–7.44 (m, 2H), 7.56–7.68 (m, 2H), 7.769 (d, 1H, J=8.3 Hz), 7.839 (d, 1H, J=8.3 Hz), 9.138 (d, 1H, J=7.8 Hz), 9.167 (d, 1H, J=8.1 Hz).

Fab-MS (m/z): 428 $(M+1)^+$

EXAMPLE 36

Synthesis of Compound 37

In 6 ml of DMF was dissolved 121 mg (0.28 mmol) of Compound 36, and 445 mg (1.70 mmol) of triphenylphosphine and 0.089 ml (1.5 mmol) of bromine were added thereto at −20° C. in an argon atmosphere, followed by stirring at room temperature overnight. Water was added to stop the reaction, and the reaction mixture was extracted with AcOEt. The extract was washed with water and then with brine and dried over $MgSO_4$. The solvent was evaporated, and the residue was purified by silica gel column chromatography (AcOEt/toluene=1/30) to give 90 mg (61%) of Compound 37.

$^1$HNMR ($CDCl_3$) δ: 2.743 (dd, 1H, J=4.4, 11.5 Hz), 3.018 (dd, 1H, J=4.6, 11.5 Hz), 3.301 (s, 3H), 4.179 (s, 3H), 5.067 (dd, 1H, J=6.8, 12.0 Hz), 5.076 (dd, 1H, J=5.4, 12.0 Hz), 5.10–5.19 (m, 1H), 7.44–7.49 (m, 2H), 7.54–7.70 (m, 4H), 9.258 (dd, 1H, J=0.7, 7.8 Hz), 9.271 (dd, 1H, J=0.7, 8.1 Hz).

Fab-MS (m/z): 519 $(M+1)^+$

EXAMPLE 37

Synthesis of Compound 38

In 3 ml of DMF was dissolved 103 mg (0.20 mmol) of Compound 37, and 0.47 ml (5.2 mmol) of a 50% aqueous dimethylamine solution was added thereto, followed by stirring at room temperature for one day. To the reaction mixture was added ice-water, and the thus formed precipitate was collected by filtration and dried under reduced pressure. The resulting crystals were purified by TLC ($CHCl_3$/MeOH/triethylamine=25/1/1). The purified product was dissolved in $CHCl_3$, and 0.88N HCl (AcOEt solution) was added thereto, followed by stirring at room temperature for 1 hour. AcOEt was added to the reaction mixture to precipitate crystals. The crystals were collected by filtration, washed with AcOEt, and dried under reduced pressure to give 57 mg (58%) of Compound 38.

$^1$HNMR (DMSO-$d_6$) δ: 2.500 (s, 6H), 2.5–2.7 (br, 2H), 3.188 (s, 3H), 4.0–4.2 (br, 1H), 4.242 (s, 3H), 4.82–4.93 (m, 2H), 5. 267 (d, 1H, J=6.6 Hz), 7.41–7.46 (m, 2H), 7.62–7.70 (m, 2H), 7.775 (d, 1H, J=8.3 Hz), 7.967 (d, 1H, J=8.3 Hz), 9.140 (d, 1H, J=7.8 Hz), 9.192 (d, 1H, J=7.8 Hz), 9.4–9.6 (br, 1H).

Fab-MS (m/z): 455 $(M+1)^+$

EXAMPLE 38

Synthesis of Compound 39

In 20 ml of dichloromethane was dissolved 112 mg (0.24 mmol) of Compound 24, and 0.125 ml (2.38 mmol) of dichloromethyl methyl ether and 2.4 ml (2.4 mmol) of 1.0M titanium tetrachloride (dichloromethane solution) were added thereto, followed by stirring at room temperature for 3 hours. The reaction was stopped by addition of a phosphate buffer (pH=7), and the reaction mixture was filtered using Celite and extracted with dichloromethane. The extract was washed successively with water and brine and dried over $MgSO_4$, and the solvent was evaporated to give 125 mg (quantitative) of Compound 39.

Fab-MS (m/z): 531 $(M+1)^+$

EXAMPLE 39

Synthesis of Compound 40

In 500 ml of dichloromethane was dissolved 126 mg (0.24 mmol) of Compound 39, and 1.11 g (3.54 mmol) of m-chloroperbenzoic acid and 295 mg (3.51 mmol) of sodium hydrogencarbonate were added thereto, followed by stirring at room temperature for 2 days. To the reaction mixture were added a phosphate buffer (pH=7) and 900 mg (7.15 mmol) of sodium sulfite to stop the reaction, and the reaction mixture was extracted with dichloromethane. The extract was dried over $MgSO_4$, and the solvent was removed by evaporation. The residue was purified by silica gel column chromatography ($CHCl_3$/MeOH=100/1). The resulting oily substance was dissolved in 4 ml of DMF, and 0.83 ml (9.2 mmol) of a 50% aqueous solution of dimethylamine was added thereto, followed by stirring at room temperature for 2 hours. The reaction mixture was diluted with water and extracted with AcOEt. The extract was washed successively with water and brine and dried over $MgSO_4$. The solvent was evaporated, and the residue was purified by TLC ($CHCl_3$/MeOH/aqueous ammonia=50/10/1). The resulting powder was dissolved in $CHCl_3$, and 0.88N HCl (AcOEt solution) was added thereto, followed by stirring at room temperature for 1 hour. The resulting precipitate was collected by filtration, washed with AcOEt, and dried under reduced pressure to yield 18 mg (16%) of Compound 40.

$^1$HNMR (DMSO-$d_6$) δ: 1.81–1.85 (m, 2H), 2.556 (s, 6H), 2.8–2.9 (br, 2H), 3.179 (s, 3H), 4.109 (s, 3H), 4.698 (t, 2H, J=7.6 Hz), 7.122 (dd, 1H, J=2.5, 8.7 Hz), 7.139 (dd, 1H, J=2.6, 8.8 Hz), 7.569 (d, 1H, J=8.7 Hz), 7.716 (d, 1H, J=8.8 Hz), 8.558 (d, 1H, J=2.5 Hz), 8.592 (d, 1H, J=2.6 Hz), 9.356 (s, 1H), 9.392 (s, 1H).

Fab-MS (m/z): 471 $(M+1)^+$

EXAMPLE 40

Synthesis of Compounds 41 and 42

In a mixed solvent of 30 ml of DMF and 60 ml of toluene was dissolved 5.15 g (13.0 mmol) of Compound 89, and 1.45 g (12.9 mmol) of potassium tert-butoxide was added thereto at −20° C. in an argon atmosphere, followed by stirring at room temperature for 30 minutes. After cooling again to −20° C., 1.12 ml (12.9 mmol) of allyl bromide was added thereto, and the mixture was stirred at 0° C. for 2 hours. The solvent was removed by evaporation under reduced pressure, and water was added to the residue. The mixture was extracted with THF, and the extract was washed with brine and dried over $MgSO_4$. The solvent was evaporated, and the residue was purified by silica gel column chromatography (AcOEt/toluene=1/15) and triturated with dichloromethane to give 555 mg (10%) of Compound 41 as a 4:1 mixture of regioisomers and 898 mg (16%) of Compound 42 as a single isomer.

Compound 41:

$^1$HNMR ($CDCl_3$) δ: 1.63–2.11 (m, 6H), 3.80–3.88 (m, 1H), 4.15–4.20 (m, 1H), 4.774 (d, 1H, J=16.6 Hz), 4.904 (d, 1H, J=16.6 Hz), 5.03–5.08 (m, 1H), 6.24–6.34 (m, 1H), 7.15–7.58 (m, 6H), 7.77–7.82 (m, 1H), 8.493 (brs, 1H), 9.227 (d, 0.8H, J=8.1 Hz), 9.409 (d, 0.2H, J=8.3 Hz).

Fab-MS (m/z): 436 $(M+1)^+$

Compound 42:

$^1$HNMR (DMSO-$d_6$) δ: 1.56–1.61 (m, 2H), 1.73–1.87 (m, 2H), 2.00–2.14 (m, 2H), 3.63–3.69 (m, 1H), 3.99–4.02 (m, 1H), 4.747 (dd, 1H, J=1.5, 17.1 Hz), 5.053 (dd, 1H, J=1.5, 10.4 Hz), 5.084 (d, 1H, J=17.3 Hz), 5.138 (d, 1H, J=17.3 Hz), 5.462 (dd, 1H, J=2.0, 11.0 Hz), 5.593 (d, 2H, J=4.6 Hz), 6.178 (ddt, 1H, J=4.6, 10.4, 17.1 Hz), 7.242 (ddd, 1H, J=0.9, 7.0, 7.9 Hz), 7.368 (dd, 1H, J=7.2, 7.8 Hz), 7.455 (ddd, 1H, J=1.2, 7.0, 8.2 Hz), 7.542 (ddd, 1H, J=1.1, 7.2, 8.3 Hz), 7.711 (dd, 1H, J=0.9, 8.2 Hz), 7.762 (d, 1H, J=8.3 Hz), 8.177 (d, 1H, J=7.8 Hz), 9.305 (d, 1H, J=7.9 Hz), 11.573 (s, 1H).

Fab-MS (m/z): 436 $(M+1)^+$

EXAMPLE 41

Synthesis of Compound 43

In 300 ml of THF was dissolved 2.05 g (4.71 mmol) of Compound 41, and 240 ml of 4N sulfuric acid was added thereto, followed by stirring at 60° C. overnight. After cooling to room temperature, ice was added to the reaction mixture, followed by extraction with AcOEt. The extract was washed successively with water and brine and dried over $MgSO_4$. The solvent was removed from the extract by evaporation, and the residue was triturated with ethyl ether and dried under reduced pressure. The resulting crystals were dissolved in a mixed solvent of 30 ml of DMF and 60 ml of toluene, and 327 mg (8.18 mmol) of 60% sodium hydride was added to the solution at 0° C. in an argon atmosphere, followed by stirring for 15 minutes. To the reaction mixture was added 0.61 ml (9.8 mmol) of methyl iodide, followed by stirring at room temperature for 2.5 hours. The solvent was evaporated under reduced pressure, and water was added to the residue. The mixture was extracted with AcOEt, and the extract was washed successively with water and brine, and dried over $MgSO_4$. The solvent was evaporated, and the residue was purified by silica gel column chromatography (AcOEt/toluene=1/8) to give 1.15 g (64%) of Compound 43 as a 4:1 mixture of regioisomers.

$^1$HNMR ($CDCl_3$) δ: 3.298 (s, 3H), 3.980 (s, 2.4H), 4.065 (s, 0.6H), 4.747 (s, 0.4H), 4.755 (s, 1.6H), 4.960 (ddd, 0.4H, J=1.9, 1.9, 3.9 Hz), 5.072 (ddd, 0.4H, J=1.9, 1.9, 3.9 Hz), 5.39–5.45 (m, 2H), 6.15–6.23 (m, 1H), 7.35–7.39 (m, 2H), 7.42–7.56 (m, 4H), 7.85–7.88 (m, 1H), 9.54–9.57 (m, 1H).

Fab-MS (m/z): 380 $(M+1)^+$

EXAMPLE 42

Synthesis of Compounds 44 and 45

In 30 ml of THF was suspended 489 mg (12.9 mmol) of sodium borohydride, and 1.59 g (6.28 mmol) of iodine was added to the suspension at 0° C. in an argon atmosphere. After stirring for 15 minutes, the mixture was added dropwise to a solution of 1.13 g (2.99 mmol) of Compound 43 in 100 ml of THF over a period of 5 minutes, and the mixture was stirred at room temperature for 5.5 hours in an argon atmosphere. The reaction mixture was cooled to 0° C., and 30 ml of a 1N aqueous solution of sodium hydroxide and 30 ml of 35% aqueous hydrogen peroxide were added thereto, followed by stirring for 30 minutes. The reaction mixture was diluted with water and extracted with AcOEt. The extract was washed successively with water and brine and dried over $MgSO_4$. The solvent was evaporated, and the residue was triturated with AcOEt to give 928 mg (78%) of Compound 45 as a 4:1 mixture of regioisomers. The filtrate was triturated with a 50:1 mixed solvent of $CHCl_3$ and MeOH to recover 125 mg (11%) of Compound 44.

Compound 45:

$^1$HNMR (DMSO-$d_6$) δ: 1.68–1.82 (m, 2H), 3.143 (t, 0.4H, J=6.1 Hz), 3.204 (t, 1.6H, J=6.1 Hz), 3.0–3.7 (br, 1H), 3.233 (s, 2.4H), 3.240 (s, 0.6H), 4.185 (s, 2.4H), 4.237 (s, 0.6H), 4.808 (t, 0.4H, J=7.8 Hz), 4.839 (t, 1.6H, J=7.6 Hz), 4.984 (s, 1.6H), 4.991 (s, 0.4H), 7.23–7.32 (m, 1H), 7.33–7.40 (m, 1H), 7.47–7.60 (m, 2H), 7.66–7.87 (m, 2H), 9.419 (ddd, 0.8H, J=0.6, 1.1, 8.0 Hz), 9.454 (d, 0.2H, J=8.0 Hz).

Fab-MS (m/z): 398 $(M+1)^+$

Compound 44:

$^1$HNMR (DMSO-$d_6$) δ: 0.687 (d, 3H, J=6.1 Hz), 3.253 (s, 3H), 3.89–3.96 (m, 1H), 4.202 (s, 3H), 4.661 (d, 1H, J=6.8 Hz), 4.670 (dd, 1H, J=5.9, 14.7 Hz), 4.845 (dd, 1H, J=7.1, 14.7 Hz), 5.029 (s, 2H), 7.297 (ddd, 1H, J=0.9, 7.0, 7.9 Hz), 7.34–7.39 (m, 1H), 7.528 (ddd, 1H, J=1.2, 7.0, 8.2 Hz), 7.542 (ddd, 1H, J=1.2, 7.0, 8.2 Hz), 7.689 (d, 1H, J=8.2 Hz), 7.867 (d, 1H, J=8.2 Hz), 8.023 (d, 1H, J=7.8 Hz), 9.408 (d, 1H, J=7.9 Hz).

Fab-MS (m/z): 398 $(M+1)^+$

EXAMPLE 43

Synthesis of Compound 46

In the same manner as in Example 23, 456 mg (47%) of Compound 46 was obtained as a 4:1 mixture of regioisomers from 835 mg (2.10 mmol) of Compound 45, 1.65 g (6.30 mmol) of triphenylphosphine, and 0.22 ml (4.3 mmol) of bromine.

$^1$HNMR ($CDCl_3$) δ: 1.97–2.10 (m, 2H), 2.877 (t, 0.4H, J=6.2 Hz), 2.959 (t, 1.6H, J=6.3 Hz), 3.347 (s, 2.4H), 3.351 (s, 0.6H), 4.125 (s, 2.4H), 4.211 (s, 0.6H), 4.857 (s, 1.6H), 4.891 (s, 0.4H), 4.894 (t, 2H, J=7.0 Hz), 7.65–7.41 (m, 2H), 7.4 6–7.58 (m, 3H), 7.61–7.66 (m, 1H), 7.89–7.93 (m, 1H), 9.529 (ddd, 0.8H, J=0.7 Hz, 1.2 Hz, 7.9 Hz), 9.554 (d, 0.2H, J=7.9 Hz).

Fab-MS (m/z): 460 $(M+1)^+$

EXAMPLE 44

Synthesis of Compound 47

In the same manner as in Example 24, 44 mg (39%) of Compound 47 was obtained as a 5:1 mixture of regioisomers from 1.25 mg of (0.27 mmol) of Compound 46, 0.10 ml (1.1 mmol) of a 50% aqueous solution of dimethylamine, and 0.88N HCl (AcOEt solution).

$^1$HNMR (free base) ($CDCl_3$) δ: 1.61–1.74 (m, 2H), 1.895 (t, 0.33H, J=6.8 Hz), 1.953 (t, 1.67H, J=6.8 Hz), 1.972 (s, 1.0H), 2.002 (s, 5.0H), 3.330 (s, 3H), 4.091 (s, 2.5H), 4.172 (s, 0.5H), 4.702 (t, 0.33H, J=7.4 Hz), 4.750 (t, 1.67H, J=7.4 Hz), 4.819 (s, 1.67H), 4.839 (s, 0.33H), 7.32–7.40 (m, 2H), 7.46–7.64 (m, 4H), 7.87–7.91 (m, 1H), 9.533 (dd, 0.83H, J=1.0, 8.0 Hz), 9.563 (dd, 0.17H, J=1.0, 8.0 Hz).

Fab-MS (m/z): 425 $(M+1)^+$

EXAMPLE 45

Synthesis of Compound 48

In the same manner as in Example 41, 1.14 g (64%) of a methylated compound was obtained from 2.05 g (4.71 mmol) of Compound 42. From 1.13 g of the resulting methylated compound was obtained 1.10 g (92%) of an alcohol compound in the same manner as in Example 22. From 835 mg of the resulting alcohol compound was obtained 456 mg (47%) of a brominated compound in the same manner as in Example 23. Compound 48 was obtained from 152 mg of the resulting brominated compound in a yield of 86 mg (82%) in the same manner as in Example 24.

$^1$HNMR (free base) ($CDCl_3$) δ: 1.67–1.72 (m, 2H), 1.772 (t, 2H, J=6.1 Hz), 1.96–1.99 (m, 4H), 3.336 (s, 3H), 3.34–3.43 (m, 4H), 4.112 (s, 3H), 4.829 (s, 2H), 4.840 (t, 2H, J=6.9 Hz), 7.34–7.40 (m, 2H), 7.470 (d, 1H, J=8.1 Hz), 7.50–7.56 (m, 2H), 7.623 (d, 1H, J=8.1 Hz), 7.890 (d, 1H, J=7.6 Hz), 9.513 (d, 1H, J=8.0 Hz).

Fab-MS (m/z): 467 $(M+1)^+$

EXAMPLE 46

Synthesis of Compound 49

In the same manner as in Example 41, 1.14 g (64%) of a methylated compound was obtained from 2.05 g (4.71 mmol) of Compound 42. From 1.13 g of the resulting methylated compound was obtained 1.10 g (92%) of an alcohol compound in the same manner as in Example 22. From 835 mg of the resulting alcohol compound was obtained 456 mg (47%) of a brominated compound in the same manner as in Example 23. Compound 49 was obtained from 152 mg of the resulting brominated compound in a yield of 348 mg (84%) in the same manner as in Example 32.

$^1$HNMR ($CDCl_3$) δ: 1.78–1.84 (m, 2H), 2.883 (t, 2H, J=6.4 Hz), 3.365 (s, 3H), 4.126 (s, 3H), 4.826 (t, 2H, J=7.1 Hz), 4.895 (s, 2H), 7.37–7.41 (m, 2H), 7.511 (d, 1H, J=7.9 Hz), 7.53–7.58 (m, 2H), 7.633 (d, 1H, J=8.2 Hz), 7.924 (d, 1H, J=7.7 Hz), 9. 534 (d, 1H, J=7.9 Hz).

Fab-MS (m/z): 423 $(M+1)^+$

EXAMPLE 47

Synthesis of Compound 50

In the same manner as in Example 33, 108 mg (87%) of Compound 50 was obtained from 133 mg (0.31 mmol) of Compound 49.

$^1$HNMR (DMSO-$d_6$) δ: 1.70–1.74 (m, 2H), 2.290 (t, 2H, J=7.0 Hz), 3.259 (s, 3H), 4.216 (s, 3H), 4.910 (t, 2H, J=6.8 Hz), 5.048 (s, 2H), 7.28–7.41 (m, 2H), 7.51–7.59 (m, 2H), 7.683 (d, 1H, J=7.6 Hz), 7.848 (d, 1H, J=8.1 Hz), 8.045 (d, 1H, J=7.8 Hz), 9.412 (d, 1H, J=8.1 Hz).

Fab-Ms (m/z): 397 $(M+1)^+$

EXAMPLE 48

Synthesis of Compound 51

In the same manner as in Example 30, 26 mg (27%) of Compound 51 was obtained from 74 mg (0.19 mmol) of Compound 50, 0.072 ml (1.0 mmol) of propanal, 65 mg (1.0 mmol) of sodium cyanoborohydride, and 0.88N HCl (AcOEt solution).

$^1$HNMR (DMSO-$d_6$) δ: 0.664 (t, 6H, J=7.3 Hz), 1.22–1.32 (m, 4H), 1.95–2.05 (m, 2H), 2.65–2.78 (m, 6H), 3.267 (s, 3H), 4.207 (s, 3H), 4.890 (t, 2H, J=7.0 Hz), 5.049 (s, 2H), 7.30–7.34 (m, 1H), 7.40–7.45 (m, 1H), 7.53–7.63 (m, 2H), 7.708 (d, 1H, J=8.3 Hz), 7.935 (d, 1H, J=8.1 Hz), 8.072 (d, 1H, J=7.6 Hz), 9.3–9.4 (br, 1H), 9.412 (d, 1H, J=8.0 Hz).

Fab-MS (m/z): 481 $(M+1)^+$

EXAMPLE 49

Synthesis of Compound 52

In the same manner as in Example 41, 1.88 g (74%) of Compound 52 was obtained from 2.37 g (6.24 mmol) of Compound 3, 400 ml of 4N sulfuric acid, 227 mg (5.68 mmol) of 60% sodium hydride, and 0.39 ml (6.3 mmol) of methyl iodide.

$^1$HNMR ($CDCl_3$) δ: 3.295 (s, 3H), 4.758 (s, 2H), 4.84–4.87 (m, 2H), 4.92–4.95 (m, 2H), 5.38–5.46 (m, 4H), 6.07–6.19 (m, 2H), 7.34–7.41 (m, 2H), 7.45–7.54 (m, 4H), 7.859 (d, 1H, J=7.6 Hz), 9.588 (d, 1H, J=8.1 Hz).

Fab-MS (m/z): 406 $(M+1)^+$

EXAMPLE 50

Synthesis of Compounds 53 and 54

In the same manner as in Example 42, 203 mg (12%) of Compound 53 and 988 mg (49%) of Compound 54 were obtained from 1.85 g (4.57 mmol) of Compound 52, 580 mg (15.34 mmol) of sodium borohydride, and 1.76 g (6.93 mmol) of iodine. Compound 53 (1.5:1 mixture of regioisomers):

$^1$HNMR (DMSO-$d_6$) δ: 1.203 (d, 1.2H, J=6.2 Hz), 1.229 (d, 1.8H, J=6.3 Hz ), 3.262 (s, 3H), 4.17–4.24 (m, 1H), 4.78–4.83 (m, 2H), 5.037 (s, 2H), 5.143 (d, 0.4H, J=4.5 Hz), 5.152 (d, 0.6H, J=4.4 Hz), 7.21–7.26 (m, 1H), 7.30–7.36 (m, 1H), 7.42–7.54 (m, 2H), 7.70–7.73 (m, 1H), 7.77–7.81 (m, 1H), 8.02–8.04 (m, 1H), 9.325 (d, 0.6H, J=8.0 Hz), 9.395 (dd, 0.4H, J=1.2 Hz, 8.0 Hz).

Fab-MS (m/z): 384 $(M+1)^+$

Compound 54:

$^1$HNMR (DMSO-$d_6$) δ: 1.60–1.66 (m, 2H), 1.69–1.75 (m, 2H), 3.02–3.07 (m, 2H), 3.09–3.13 (m, 2H), 3.259 (s, 3H), 4.370 (t, 1H, J=5.0 Hz), 4.422 (t, 1H, J=5.0 Hz), 4.777 (t, 2H, J=7.4 Hz), 4.816 (t, 2H, J=7.4 Hz), 5.054 (s, 2H), 7.290 (ddd, 1H, J=0.8 Hz, 7.1 Hz, 7.9 Hz), 7.383 (ddd, 1H, J=0.8, 7.1, 7.9 Hz), 7.507 (ddd, 1H, J=1.2, 7.1, 8.3 Hz), 7.561 (ddd, 1H, J=1.2, 7.1, 8.3 Hz), 7.781 (d, 1H, J=8.3 Hz), 7.853 (d, 1H, J=8.3Hz), 8.036 (d, 1H, J=7.9 Hz), 9.436 (dd, 1H, J=1.2, 7.9 Hz).

Fab-MS (m/z): 442 $(M+1)^+$

EXAMPLE 51

Synthesis of Compound 55

In the same manner as in Example 23, 624 mg (52%) of Compound 55 was obtained from 943 mg (2.14 mmol) of Compound 54, 3.36 g (12.8 mmol) of triphenylphosphine, and 0.44 ml (8.5 mmol) of bromine.

$^1$HNMR ($CDCl_3$) δ: 1.88–1.96 (m, 2H), 1.97–2.05 (m, 2H), 2.800 (t, 2H, J=6.3 Hz), 2.901 (t, 2H, J=6.3 Hz), 3.385 (s, 3H), 4.821 (t, 2H, J=6.9 Hz), 4.876 (t, 2H, J=7.1 Hz), 4.946 (s, 2H), 7.36–7.42 (m, 2H), 7.50–7.61 (m, 3H), 7.670 (d, 1H, J=8.0 Hz), 7.939 (dd, 1H, J=1.2, 7.8 Hz), 9.532 (ddd, 1H, J=0.7, 1.2, 7.8 Hz).

Fab-MS (m/z): 566 $(M+1)^+$

EXAMPLE 52

Synthesis of Compound 56

In the same manner as in Example 24, 92 mg (64%) of Compound 56 was obtained from 143 mg (0.25 mmol) of Compound 55, 0.17 ml (1.5 mmol) of a 40% aqueous solution of dimethylamine, and 0.88N HCl (AcOEt solution).

$^1$HNMR (free base) ($CDCl_3$) δ: 1.54–1.69 (m, 4H), 1.861 (t, 2H, J=6.9 Hz), 1.926 (t, 2H, J=6.9 Hz), 1.947 (s, 6H), 1.982 (s, 6H), 3.384 (s, 3H), 4.691 (t, 2H, J=7.4 Hz), 4.744 (t, 2H, J=7.5 Hz), 4.944 (s, 2H), 7.361 (ddd, 1H, J=1.0, 7.0, 8.0 Hz), 7.368 (ddd, 1H, J=0.9, 7.0, 7.9 Hz), 7.505 (ddd, 1H, J=1.2, 7.0, 8.2 Hz), 7.528 (ddd, 1H, J=1.2, 7.0, 8.2 Hz), 7.594 (d, 1H, J=8.2 Hz), 7.659 (d, 1H, J=8.2 Hz), 7.932 (d, 1H, J=7.9 Hz), 9.544 (dd, 1H, J=1.2, 8.0 Hz).

Fab-MS (m/z): 496 $(M+1)^+$

EXAMPLE 53

Synthesis of Compound 57

In the same manner as in Example 28, 99 mg (80%) of Compound 57 was obtained from 108 mg (0.19 mmol) of Compound 55, 0.067 ml (0.77 mmol) of morpholine, and 0.88N HCl (AcOEt solution).

$^1$HNMR (free base) ($CDCl_3$) δ: 1.51–1.62 (m, 4H), 1.64–1.76 (m, 4H), 1.89–1.97 (m, 8H), 3.32–3.42 (m, 8H), 3.384 (s, 3H), 4.783 (t, 2H, J=6.7 Hz), 4.842 (t, 2H, J=6.8 Hz), 4.937 (s, 2H), 7.33–7.39 (m, 2H), 7.47–7.59 (m, 3H), 7.638 (d, 1H, J=8.3 Hz), 7.929 (d, 1H, J=7.5 Hz), 9.519 (d, 1H, J=7.5 Hz).

Fab-MS (m/z): 580 $(M+1)^+$

EXAMPLE 54

Synthesis of Compound 58

In the same manner as in Example 32, 178 mg (quantitative) of Compound 58 was obtained from 201 mg (0.36 mmol) of Compound 55 and 142 mg (2.18 mmol) of sodium azide.

$^1$HNMR ($CDCl_3$) δ: 1.63–1.69 (m, 2H), 1.71–1.78 (m, 2H), 2.701 (t, 2H, J=6.4 Hz), 2.828 (t, 2H, J=6.4 Hz), 3.384 (s, 3H), 4.724 (t, 2H, J=7.0 Hz), 4.777 (t, 2H, J=7.1 Hz), 4.943 (s, 2H), 7.391 (ddd, 1H, J=0.9, 7.0, 7.9 Hz), 7.397 (ddd, 1H, J=0.9, 7.0, 7.9 Hz), 7.532 (ddd, 1H, J=1.2, 7.0, 8.2 Hz), 7.561 (ddd, 1H, J=1.2, 7.0, 8.2 Hz), 7.578 (dd, 1H, J=0.9, 8.2 Hz), 7.651 (d, 1H, J=8.2 Hz), 7.939 (dd, 1H, J=1.2, 7.9 Hz), 9.54 6 (ddd, 1H, J=0.6, 1.2, 7.9 Hz).

Fab-MS (m/z): 492 $(M+1)^+$

EXAMPLE 55

Synthesis of Compound 59

In the same manner as in Example 33, 107 mg (69%) of Compound 59 was obtained from 172 mg (0.35 mmol) of Compound 58.

$^1$HNMR (DMSO-$d_6$) δ: 1.49–1.64 (m, 4H), 2.114 (t, 2H, J=6.9 Hz), 2.161 (t, 2H, J=6.6 Hz), 3.1–3.4 (br, 4H), 3.258 (s, 3H), 4.758 (t, 2H, J=7.1 Hz), 4.801 (t, 2H, J=7.1 Hz), 5.057 (s, 2H), 7.297 (ddd, 1H, J=0.8 Hz, 7.0 Hz, 7.8 Hz), 7.388 (ddd, 1H, J=0.7 Hz, 7.1 Hz, 7.8 Hz), 7.514 (ddd, 1H, J=1.2 Hz, 7.0 Hz, 8.2 Hz), 7.569 (ddd, 1H, J=1.1 Hz, 7.1 Hz, 8.2 Hz), 7.811 (d, 1H, J=8.2 Hz), 7.881 (d, 1H, J=8.2 Hz), 8.041 (d, 1H, J=7.8 Hz), 9.429 (d, 1H, J=7.8 Hz).

Fab-MS (m/z): 440 $(M+1)^+$

EXAMPLE 56

Synthesis of Compounds 60 and 61

In the same manner as in Example 42, 88 mg (61%) of Compound 60 and 37 mg (25%) of Compound 61 were obtained from 137 mg (0.29 mmol) of Compound 3, 78 mg (2.05 mmol) of sodium borohydride, and 231 mg (0.91 mmol) of iodine. Compound 60:

$^1$HNMR ($CDCl_3$) δ: 1.60–2.11 (m, 10H), 3.129 (t, 2H, J=5.9 Hz), 3.192 (t, 2H, J=5.9 Hz), 3.798 (dt, 1H, J=2.8, 11.7 Hz), 4.09–4.15 (m, 1H), 4.723 (t, 2H, J=7.2 Hz), 4.807 (t, 2H, J=7.2 Hz), 4.943 (d, 1H, J=16.6 Hz), 5.107 (d, 1H, J=16.6 Hz), 5.652 (dd, 1H, J=2.4, 10.5 Hz), 7.15–7.18 (m, 1H), 7.318 (ddd, 1H, J=1.1, 7.0, 8.0 Hz), 7.35–7.39 (m, 1H), 7.461 (ddd, 1H, J=1.2, 6.8, 8.0 Hz), 7.519 (dd, 1H, J=1.0, 8.0 Hz), 7.610 (d, 1H, J=8.0 Hz), 7.951 (d, 1H, J=8.0 Hz), 9.490 (d, 1H, J=8.0 Hz).

Fab-Ms (m/z): 512 $(M+1)^+$

Compound 61:

$^1$HNMR (DMSO-$d_6$) δ: 1.236 (s, 2H), 1.37–1.44 (m, 2H), 1.50–1.56 (m,2H), 1.59–1.66 (m, 2H), 1.69–1.81 (m, 4H), 3.046 (t, 2H, J=6.2 Hz), 3.111 (t, 2H, J=6.2 Hz), 3.2–3.4 (br, 1H), 3.427 (t, 2H, J=6.5 Hz), 3.689 (t, 2H, J=7.1 Hz), 4.779 (t, 2H, J=7.4 Hz), 4.818 (t, 2H, J=7.4 Hz), 5.059 (s, 2H), 7.287 (dd, 1H, J=7.1 Hz, 7.8 Hz), 7.382 (dd, 1H, J=7.1 Hz, 7.7 Hz), 7.508 (dd, 1H, J=7.1 Hz, 8.3 Hz), 7.563 (dd, 1H, J=7.1 Hz, 8.3 Hz), 7.782 (d, 1H, J=8.3 Hz), 7.853 (d, 1H, J=8.3 Hz), 8.086 (d, 1H, J=7.7 Hz), 9.441 (d, 1H, J=7.8 Hz).

Fab-MS (m/z): 514 $(M+1)^+$

EXAMPLE 57

Synthesis of Compound 62

In the same manner as in Example 42, 876 mg (32%) of Compound 62 was obtained as a 2:1 mixture of regioisomers from 285 mg (0.60 mmol) of Compound 3, 377 mg (9.96 mmol) of sodium borohydride, and 753 mg (2.97 mmol) of iodine.

$^1$HNMR (DMSO-$d_6$) δ: 1.199 (d, 1.0H, J=6.4 Hz), 1.224 (d, 2.0H, J=6.4 Hz), 1.35–1.45 (m, 2H), 1.49–1.57 (m, 2H), 1.74–1.83 (m, 2H), 3.2–3.4 (br, 1H), 3.426 (t, 2H, J=6.4 Hz), 3.698 (t, 2H, J=7.1 Hz), 4.18–4.24 (m, 1H), 4.79–4.83 (m, 2H), 5.1–5.2 (br, 1H), 7.21–7.26 (m, 1H), 7.30–7.36 (m, 1H), 7.42–7.54 (m, 2H), 7.70–7.82 (m, 2H), 8.08 (d, 1H, J=7.5 Hz), 9.347 (d, 0.67H, J=7.8 Hz), 9.401 (d, 0.33H, J=7.9 Hz), 11.348 (s, 0.67H), 11.514 (s, 0.33H).

Fab-MS (m/z): 456 $(M+1)^+$

EXAMPLE 58

Synthesis of Compound 63

In the same manner as in Example 22, 850 mg (57%) of Compound 63 was obtained as a 1:1.5 mixture of regioisomers from 1.44 g (3.30 mmol) of Compound 41 and 4.05 g (33.2 mmol) of a 9-BBN dimer.

$^1$HNMR (DMSO-$d_6$) δ: 1.5–1.6 (br, 2H), 1.7–1.9 (br, 2H), 2.0–2.2 (br, 2H), 2.08–2.14 (m, 2H), 3.49–3.53 (m, 2H), 3.62–3.68 (m, 2H), 3.99–4.02 (m, 2H), 5.03–5.16 (m, 3H), 5.44–5.48 (m, 1H), 7.23–7.27 (m, 1H), 7.34–7.38 (m, 1H), 7.44–7.58 (m, 2H), 7.68–7.84 (m, 2H), 8.15–8.17 (m, 1H), 9.311 (d, 0.4H, J=7.9 Hz), 9.341 (d, 0.6H, J=7.9 Hz), 11. 684 (s, 0.4H), 11.840 (s, 0.6H).

Fab-MS (m/z): 454 $(M+1)^+$

EXAMPLE 59

Synthesis of Compound 64

In the same manner as in Example 23, 179 mg (26%) of Compound 64 was obtained as a 1:1.5 mixture of regioisomers from 613 mg (1.35 mmol) of Compound 63, 1.07 g (4.09 mmol) of triphenylphosphine, and 0.21 ml (4.1 mmol) of bromine.

$^1$HNMR ($CDCl_3$) δ: 1.66–2.02 (m, 6H), 2.04–2.08 (m, 2H), 3.573 (t, 1.2H, J=5.4 Hz), 3.599 (t, 0.8H, J=5.4 Hz), 3.81–3.89 (m, 1H), 4.10–4.20 (m, 1H), 4.71–4.98 (m, 4H), 5.64–5.71 (m, 1H), 7.13–7.64 (m, 6H), 7.78–7.86 (m, 1H), 8.979 (s, 0.6H), 9.025 (s, 0.4H), 9.385 (d, 0.4H, J=8.5 Hz), 9.406 (d, 0.6H, J=8.1 Hz).

Fab-MS (m/z): 516 $(M+1)^+$

EXAMPLE 60

Synthesis of Compound 65

In 5 ml of DMF was dissolved 174 mg (0.38 mmol) of Compound 64, and 0.28 ml (3.1 mmol) of a 50% aqueous solution of dimethylamine was added thereto, followed by stirring at room temperature for 3 hours. To the reaction mixture was added ice-water, and the thus formed precipitate was collected by filtration and dried under reduced pressure. The residue was purified by TLC ($CHCl_3$/MeOH= 25/1) to yield 81 mg (44%) of Compound 60 as a 1:1.5 mixture of regioisomers.

$^1$HNMR ($CDCl_3$) δ: 1.61–2.03 (m, 6H), 2.07–2.12 (m, 2H), 2.467 (s, 2.4H), 2.506 (s, 3.6H), 2.59–2.65 (m, 2H), 3.69–3.86 (m, 1H), 4.04–4.16 (m, 1H), 4.87–4.97 (m, 2H), 4.911 (d, 0.4H, J=16.6 Hz), 5.009 (d, 0.6H, J=16.6 Hz), 5.127 (d, 0.4H, J=16.6 Hz), 5.140 (d, 0.6H, J=16.6 Hz), 5.66–5.70 (m, 1H), 7.23–7.54 (m, 6H), 7.5–7.8 (br, 1H), 7.99–8.04 (m, 1H), 9.479 (d, 0.4H, J=8.1 Hz), 9. 533 (dd, 1H, J=0.8, 8.1 Hz).

Fab-MS (m/z): 481 $(M+1)^+$

EXAMPLE 61

Synthesis of Compounds 66 and 67

In a mixed solvent of 10 ml of DMF and 20 ml of toluene was dissolved 1.55 g (3.93 mmol) of Compound 89, and 332 mg (8.31 mmol) of 60% sodium hydride was added thereto at 0° C. in an argon atmosphere, followed by stirring for 15 minutes. To the reaction mixture was added 2.20 ml (19.8 mmol) of ethyl bromoacetate, and the mixture was stirred at room temperature for 2.5 hours. The solvent was evaporated under reduced pressure, and water was added to the residue. The mixture was extracted with AcOEt, and the extract was washed successively with water and brine and dried over $MgSO_4$. The solvent was evaporated, and the residue was purified by silica gel column chromatography (AcOEt/toluene=1/9) to give 672 mg (30%) of Compound 66 and 615 mg (33%) of Compound 67.

Compound 66:

$^1$HNMR ($CDCl_3$) δ: 1.290 (t, 3H, J=7.1 Hz), 1.311 (t, 3H, J=7.1 Hz), 1.62–2.11 (m, 6H), 3.809 (dt, 1H, J=2.5, 11.7 Hz), 4.118 (dt, 1H, J=2.3, 11.7 Hz), 4.310 (q, 2H, J=7.1 Hz), 4.319 (q, 2H, J=7.1 Hz), 4.984 (d, 1H, J=16.4 Hz), 5.057 (s, 2H), 5.146 (d, 1H, J=16.4 Hz), 5.171 (s, 2H), 5.658 (dd, 1H, J=2.5, 10.6 Hz), 7.327 (d, 1H, J=8.1 Hz), 7.37–7.43 (m, 2H), 7.4 6–7.55 (m, 2H), 7.980 (d, 1H, J=7.7 Hz), 9.516 (d, 1H, J=7.8 Hz).

Fab-MS (m/z): 568 $(M+1)^+$

Compound 67 (2.5:1 mixture of regioisomers):

$^1$HNMR (DMSO-$d_6$) δ: 1.150 (t, 0.86H, J=7.2 Hz), 1.165 (t, 2.14H, J=7.2 Hz), 1.56–1.64 (m, 2H), 1.71–1.88 (m, 2H), 1.98–2.15 (m, 2H), 3.63–3.69 (m, 1H), 3.99–4.06 (m, 1H), 4.126 (q, 0.57H, J=7.2 Hz), 4.143 (q, 1.43H, J=7.2 Hz), 5.086 (d, 1H, J=17.3 Hz), 5.135 (d, 0.29H, J=17.3 Hz), 5.140 (d, 0.71H, J=17.3 Hz), 5.45–5.48 (m, 1H), 5.830 (s, 0.57H), 5.863 (s, 1.43H), 7.23–7.41 (m, 2H), 7.42–7.56 (m, 2H), 7.63–7.74 (m, 2H), 8.15–8.18 (m, 1H), 9.305 (d, 0.71H, J=7.9 Hz), 9.355 (d, 0.29H, J=7.9 Hz), 11.668 (s, 0.71H), 11.836 (s, 0.29H).

Fab-MS (m/z): 482 $(M+1)^+$

EXAMPLE 62

Synthesis of Compound 68

In 30 ml of THF was dissolved 288 mg (0.60 mmol) of Compound 67, and 48 mg (1.27 mmol) of lithium aluminum hydride was added thereto at 0° C. in an argon atmosphere, followed by stirring for 30 minutes. A small amount of water was added to the reaction mixture to stop the reaction. The reaction mixture was heated under reflux and filtered using Celite. The filtrate was concentrated and purified by silica gel column chromatography (AcOEt/toluene=1/2) to give 177 mg (68%) of Compound 68 as a 2.5:1 mixture of regioisomers.

$^1$HNMR (DMSO-$d_6$) δ: 1.5–1.7 (br, 2H), 1.7–1.9 (br, 2H), 2.01–2.14 (m, 2H), 3.63–3.69 (m, 1H), 3.92–4.02 (m, 1H), 4.94–5.00 (m, 3H), 5.070 (d, 1H, J=17.3 Hz), 5.107 (0.71H, J=17.3 Hz), 5.114 (d, 0.29H, J=17.3 Hz), 5.45–5.48 (m, 1H), 7.22–7.27 (m, 1H), 7.31–7.37 (m, 1H), 7.43–7.55 (m, 2H), 7.71–7.82 (m, 2H), 8. 143 (d, 1H, J=7.7 Hz), 9.305 (d, 0.71H, J=8.0 Hz), 9.350 (d, 0.29H, J=7.9 Hz), 11.462 (s, 0.71H), 11.636 (s, 0.29H).

Fab-MS (m/z): 440 $(M+1)^+$

EXAMPLE 63

Synthesis of Compound 63

In the same manner as in Example 23, 85 mg (42%) of a brominated compound was obtained from 177 mg (0.40 mmol) of Compound 68. From 82 mg of the resulting brominated compound was obtained 65 mg (80%) of an azide compound in the same manner as in Example 32. Compound 69 was obtained from 60 mg of the resulting azide compound as a 2:1 mixture of regioisomers in a yield of 25 mg (45%).

$^1$HNMR ($CDCl_3$) δ: 1.61–2.08 (m, 6H), 3. 308 (t, 0.67H, J=5.3 Hz), 3.367 (t, 1.33H, J=5.3 Hz), 3.7 6–3.84 (m, 1H), 4.08–4.15 (m, 1H), 4.51–4.64 (m, 2H), 4.686 (d, 0.33H, J=16.6 Hz), 4.771 (d, 0.67H, J=16.4 Hz), 4.845 (d, 0.33H, J=16.6 Hz), 4.925 (d, 0.67H, J=16.4 Hz), 5.57–5.63 (m, 1H), 7.17–7.61 (m, 6H), 7.777 (d, 0.33H, J=7.5 Hz), 7.812 (d, 0.67H, J=7.9 Hz), 9.353 (d, 0.67H, J=8.3 Hz), 9.374 (d, 0.33H, J=8.5 Hz), 11.3–11.6 (br, 1H), 11.3–12.0 (br, 2H).

Fab-MS (m/z): 439 $(M+1)^+$

EXAMPLE 64

Synthesis of Compound 70

In the same manner as in Example 61, 221 mg (63%) of Compound 70 was obtained as a 4:1 mixture of regioisomers from 280 mg (0.86 mmol) of Compound 80 described in Reference Example 1, 51 mg (1.27 mmol) of 60% sodium hydride, and 0.19 ml (1.71 mmol) of ethyl bromoacetate.

$^1$HNMR (DMSO-$d_6$) δ: 1.153 (t, 0.6H, J=7.1 Hz), 1.165 (t, 2.4H, J=7.1 Hz), 3.266 (s, 2.4H), 3.280 (s, 0.6H), 4.126 (q, 0.4H, J=7.1 Hz), 4.140 (q, 1.6H, J=7.1 Hz), 5.049 (s, 2H), 5.801 (s, 0.4H), 5.839 (s, 1.6H), 7.21–7.73 (m, 6H), 8.035 (d, 0.2H, J=7.8 Hz), 8.044 (d, 0.8H, J=7.6 Hz), 9.342 (d, 0.8H, J=8.1 Hz), 9.395 (d, 0.2H, J=8.0 Hz), 11.605 (s, 0.8H), 11.761 (s, 0.2H).

Fab-MS (m/z): 412 $(M+1)^+$

EXAMPLE 65

Synthesis of Compound 71

In the same manner as in Example 62, 133 mg (68%) of Compound 71 was obtained as a 4:1 mixture of regioisomers from 216 mg (0.53 mmol) of Compound 70 and 41.0 mg (1.08 mmol) of lithium aluminum hydride.

$^1$HNMR (DMSO-$d_6$) δ: 3.263 (s, 2.4H), 3.269 (s, 0.6H), 3.94–3.95 (m, 2H), 4.960 (t, 1.6H, J=5.4 Hz), 4.992 (t, 0.4H, J=5.4 Hz), 5.035 (s, 2H), 7.21–7.26 (m, 1H), 7.30–7.36 (m, 1H), 7.42–7.54 (m, 2H), 7.70–7.74 (m, 1H), 7.776 (d, 0.2H, J=8.2 Hz), 7.799 (d, 0.8H, J=8.3 Hz), 8.032 (d, 1H, J=7.7 Hz), 9.340 (d, 0.8H, J=8.0 Hz), 9.386 (d, 0.2H, J=7.7 Hz), 11.418 (s, 0.8H), 11.578 (s, 0.2H).

Fab-MS (m/z): 370 $(M+1)^+$

EXAMPLE 66

Synthesis of Compound 72

In the same manner as in Example 23, 80 mg (68%) of Compound 72 was obtained as a 4:1 mixture of regioisomers from 100 mg (0.27 mmol) of Compound 71, 219 mg (0.83 mmol) of triphenylphosphine, and 0.040 ml (0.78 mmol) of bromine.

$^1$HNMR ($CDCl_3$) δ: 3.100 (s, 2.4H), 3.111 (s, 0.6H), 3.508 (t, 0.4H, J=7.1 Hz), 3.682 (t, 1.6H, J=7.1 Hz), 4.069 (s, 0.4H), 4.225 (s, 1.6H), 4.744 (t, 2H, J=7.1 Hz), 7.29–7.58 (m, 6H), 7.68–7.74 (m, 1H), 8.077 (s, 0.8H), 9.055 (s, 0.2H), 9.476 (d, 0.8H, J=8.1 Hz), 9.517 (d, 0.2H, J=8.1 Hz).

Fab-MS (m/z): 432 $(M+1)^+$

EXAMPLE 67

Synthesis of Compound 73

In the same manner as in Example 24, 18 mg (22%) of Compound 73 was obtained as a 4:1 mixture of regioisomers from 80 mg (0.19 mmol) of Compound 72, 0.13 ml (1.4 mmol) of 50% aqueous solution of dimethylamine, and 0.88N HCl (AcOEt solution).

$^1$HNMR (DMSO-$d_6$) δ: 2.942 (s, 4.8H), 2.952 (s, 1.2H), 3.244 (s, 0.6H), 3.269 (s, 2.4H), 3.55–3.60 (m, 2H), 5.000 (s, 0.4H), 5.056 (s, 1.6H), 5.368 (t, 2H, J=7.9 Hz), 7.24–7.33 (m, 1H), 7.34–7.43 (m, 1H), 7.45–7.51 (m, 1H), 7.52–7.63 (m, 1H), 7.78–7.86 (m, 1H), 7.84–7.95 (m, 1H), 8.06–8.11 (m, 1H), 9.359 (d, 0.8H, J=7.9 Hz), 9.425 (d, 0.2H, J=7.9 Hz), 10.8–10.9 (br, 1H), 11.88 (s, 1H).

Fab-MS (m/z): 397 $(M+1)^+$

EXAMPLE 68

Synthesis of Compound 74

In a mixed solvent of 15 ml of THF and 5 ml of water was dissolved 96 mg (0.17 mmol) of Compound 66, and 28 mg (0.67 mmol) of lithium hydroxide monohydrate was added thereto, followed by stirring at room temperature for one day. The solvent was evaporated under reduced pressure, and the residue was dissolved in water and adjusted to pH 1 with 1N hydrochloric acid. The resulting precipitate was collected by filtration and dried under reduced pressure. The resulting crystals were dissolved in 5 ml of MeOH, and 38 mg (0.34 mmol) of potassium tert-butoxide was added thereto, followed by stirring at room temperature for 30 minutes. The solvent was evaporated under reduced pressure, and the residue was triturated with ethyl ether to yield 92 mg (93%) of Compound 74.

$^1$HNMR (DMSO-$d_6$) δ: 1.50–1.66 (m, 2H), 1.70–1.89 (m, 2H), 1.93–2.15 (m, 2H), 3.62–3.68 (m, 1H), 3.99–4.02 (m, 1H), 4.914 (s, 2H), 4.989 (s, 2H), 5.048 (d, 1H, J=17.2 Hz), 5.098 (d, 1H, J=17.2 Hz), 5.412 (dd, 1H, J=1.9 Hz, 11.1 Hz), 7.20–7.35 (m, 2H), 7.40–7.48 (m, 4H), 8.102 (d, 1H, J=7.8 Hz), 9.344 (dd, 1H, J=0.9 Hz, 7.9 Hz).

Fab-MS (m/z): 588 $(M+1)^+$

EXAMPLE 69

Synthesis of Compound 75

In the same manner as in Example 68, 60 mg (56%) of Compound 75 was obtained as a 1.5:1 mixture of regioisomers from 106 mg (0.22 mol) of Compound 67, 19 mg (0.45 mmol) of lithium hydroxide monohydrate, and 19 mg ( 0.17 mmol) of potassium tert-butoxide.

$^1$HNMR (DMSO-$d_6$) δ: 1.55–1.61 (m, 2H), 1.73–1.88 (m, 2H), 2.00–2.11 (m, 2H), 3.61–3.69 (m, 1H), 3.99–4.02 (m, 1H), 4.972 (s, 0.8H), 5.012 (s, 1.2H), 5.058 (d, 0.6H, J=17.3 Hz), 5.058 (d, 0.4H, J=17.8 Hz), 5.104 (d, 0.6H, J=17.3 Hz), 5.111 (d, 0.4H, J=17.8 Hz), 5.44–5.47 (m, 1H), 7.18–7.33

(m, 2H), 7.39–7.53 (m, 2H), 7.64–7.72 (m, 2H), 8.11–8.15 (m, 1H), 9.243 (d, 0.6H, J=7.8 Hz), 9.262 (d, 0.4H, J=7.3 Hz).

Fab-MS (m/z): 492 $(M+1)^+$

EXAMPLE 70

Synthesis of Compound 76

In a mixed solvent of 6 ml of DMF and 12 ml of toluene was dissolved 877 mg (2.57 mmol) of Compound 93, and 286 mg (2.55 mol) of potassium tert-butoxide was added thereto at −20° C. in an argon atmosphere, followed by stirring for 20 minutes. To the reaction mixture was further added 0.23 ml (2.7 mmol) of allyl bromide, followed by stirring at 0° C. for 2 hours. The solvent was removed under reduced pressure, and the residue was diluted with water and then extracted with AcOEt. The extract was purified by silica gel column chromatography (toluene/AcOEt=15/1) to give 512 mg (52%) of an allyl compound.

In a mixed solvent of 4 ml of DMF and 8 ml of toluene was dissolved 447 mg (1.17 mmol) of the obtained allyl compound, and 197 mg (1.76 mmol) of potassium tert-butoxide was added to the solution at 0° C. in an argon atmosphere, followed by stirring for 20 minutes. To the reaction mixture was added 0.11 ml (1.8 mmol) of methyl iodide, followed by stirring at 0° C. for 2 hours. The solvent was evaporated under reduced pressure, and the residue was diluted with water and then extracted with AcOEt. The organic layer was washed successively with water and brine and dried over $MgSO_4$. The solvent was removed by evaporation under reduced pressure, and the residue was purified by silica gel column chromatography (toluene/AcOEt=20/1) to give 225 mg (49%) of a methylated compound.

An alcohol compound was obtained from 223 mg of the resulting methylated compound in a yield of 122 mg (52%) in the same manner as in Example 22.

In the same manner as in Example 23, 69 mg (51%) of a brominated compound was obtained from 116 mg of the resulting alcohol compound.

In the same manner as in Example 24, 41 mg (62%) of Compound 76 was obtained from 66 mg of the resulting brominated compound.

$^1$HNMR (DMSO-$d_6$) δ: 2.07–2.16 (m, 2H), 2.720 (s, 6H), 3.019 (t, 2H, J=7.8 Hz), 3.061 (s, 3H), 3.878 (s, 3H), 4.312 (t, 2H, J=7.1 Hz), 6.65–6.67 (m, 2H), 6.753 (dd, 1H, J=7.3 Hz, 8.3 Hz), 6.967 (d, 1H, J=8.0 Hz), 7.03–7.11 (m, 2H), 7.442 (d, 1H, J=8.3 Hz), 7.538 (d, 1H, J=8.3 Hz), 7.761 (s, 1H), 7.879 (s, 1H), 9.9–10.0 (br, 1H).

Fab-MS (m/z): 441 $(M+1)^+$

EXAMPLE 71

Synthesis of Compound 77

In 5 ml of DMF was dissolved 177 mg (0.52 mmol) of Compound 93, and 177 mg (1.57 mmol) of potassium tert-butoxide was added thereto at 0° C. in an argon atmosphere, followed by stirring for 15 minutes. To the reaction mixture was added 0.19 ml (1.57 mmol) of benzyl bromide, followed by stirring at room temperature for 1 hour. The solvent was evaporated under reduced pressure, and water was added to the residue, followed by extraction with AcOEt. The extract was washed successively with water and brine and dried over $MgSO_4$. The solvent was evaporated, and the residue was purified by silica gel column chromatography (AcOEt/hexane=1/3) to give 181 mg (67%) of Compound 77.

$^1$HNMR ($CDCl_3$) δ: 3.180 (s, 3H), 5.351 (s, 4H), 6.729 (ddd, 2H, J=1.0, 7.1, 8.1 Hz), 6.992 (dd, 2H, J=1.0, 8.1 Hz), 7.028 (ddd, 2H, J=1.0, 7.1, 8.1 Hz), 7.11–7.14 (m, 4H), 7.212 (d, 2H, J=8.1 Hz), 7.26–7.33 (m, 6H), 7.720 (s, 2H).

Fab-MS (m/z): 522 $(M+1)^+$

EXAMPLE 72

Synthesis of Compound 78

In the same manner as in Example 71, 289 mg (82%) of Compound 78 was obtained from 197 mg (0.58 mmol) of Compound 93, 192 mg (1.71 mmol) potassium tert-butoxide, and 371 mg (1.72 mmol) of p-nitrobenzyl bromide.

$^1$HNMR ($CDCl_3$) δ: 3.193 (s, 3H), 5.459 (s, 4H), 6.772 (ddd, 2H, J=1.0, 7.0, 8.0 Hz), 7.018 (d, 2H, J=8.1 Hz), 7.081 (ddd, 2H, J=1.0, 7.0, 8.1 Hz), 7.127 (d, 2H, J=8.0 Hz), 7.240 (d, 4H, J=8.8 Hz), 7.739 (s, 2H), 8.164 (d, 4H, J=8.8 Hz).

Fab-MS (m/z): 612 $(M+1)^+$

EXAMPLE 73

Synthesis of Compound 79

In 20 ml of THF was dissolved 289 mg (0.47 mmol) of Compound 78, and 26 mg of platinum dioxide was added thereto, followed by stirring at room temperature for 2 hours in a hydrogen atmosphere. The reaction mixture was filtered using Celite, and the solvent was removed by evaporation. The residue was purified by silica gel column chromatography ($CHCl_3$/MeOH=25/1). The purified product was dissolved in $CHCl_3$, and 0.88N HCl (AcOEt solution) was added thereto, followed by stirring at room temperature for 1 hour. The resulting precipitate was collected by filtration and triturated with isopropyl alcohol under heating to give 129 mg (44%) of Compound 79.

$^1$HNMR (free base) ($CDCl_3$) δ: 3.162 (s, 3H), 5.188 (s, 4H), 6.591 (d, 4H, J=8.7 Hz), 6.709 (ddd, 2H, J=1.0, 7.0, 8.0 Hz), 6.930 (d, 4H, J=8.7 Hz), 6.963 (dd, 2H, J=1.0, 8.0 Hz), 7.027 (ddd, 2H, J=1.0, 7.0, 8.0 Hz), 7.244 (dd, 2H, J=1.0, 8.0 Hz), 7.650 (s, 2H).

Fab-MS (m/z): 552 $(M+1)^+$

EXAMPLE 74

Synthesis of Compound 94

In the same manner as in Example 24, 46 mg (87%) of Compound 94 was obtained from 156 mg (0.329 mmol) of Compound 24, 0.28 ml (3.3 mmol) of isopropylamine, and 0.88N HCl (AcOEt solution).

$^1$HNMR (DMSO-$d_6$) δ: 1.046 (d, 6H, J=6.6 Hz), 1.76–1.83 (m, 2H), 2.69–2.75 (m, 2H), 3.04–3.12 (m, 1H), 3.194 (s, 3H), 4.260 (s, 3H), 4.871 (t, 2H, J=7.7 Hz), 7.44–7.48 (m, 2H), 7.686 (ddd, 1H, J=1.2 Hz, 7.1 Hz, 8.3 Hz), 7.693 (ddd, 1H, J=1.2 Hz, 7.1 Hz, 8.3 Hz), 7.810 (d, 1H, J=8.3 Hz), 7.959 (d, 1H, J=8.3 Hz), 8.16–8.29 (m, 2H), 9.154 (br d, 1H, J=7.8 Hz), 9.188 (br d, 1H, J=7.7 Hz).

Fab-MS (m/z): 452 $(M+1)^+$

EXAMPLE 75

Synthesis of Compound 95

In the same manner as in Example 30, 80 mg (79%) of Compound 95 was obtained from 93 mg (0.21 mmol) of a free base of Compound 94, 0.34 ml (4 mmol) of a 35% formaldehyde aqueous solution, 252 mg (4.00 mmol) of sodium cyanoborohydride, and 0.88N HCl (AcOEt solution).

$^1$HNMR (DMSO-$d_6$) δ: 1.028 (d, 3H, J=6.6 Hz), 1.073 (d, 3H, J=6.6 Hz), 1.90–2.01 (m, 2H), 2.422 (d, 3H, J=5.0 Hz), 2.81–2.95 (m, 2H), 3.174 (s, 3H), 3.23–3.35 (m, 1H), 4.246 (s, 3H), 4.80–4.85 (m, 2H), 7.43–7.47 (m, 2H), 7.674 (ddd, 1H, J=1.2 Hz, 7.1 Hz, 8.3 Hz), 7.684 (ddd, 1H, J=1.2 Hz, 7.1 Hz, 8.3 Hz), 7.790 (d, 1H, J=8.3 Hz), 7.968 (d, 1H, J=8.3 Hz), 9.143 (br d, 1H, J=7.9 Hz), 9.176 (br d, 1H, J=7.9 Hz), 9.53–9.64 (br s, 1H).

Fab-MS (m/z): 467 $(M+1)^+$

EXAMPLE 76

Synthesis of Compound 96

In the same manner as in Example 24, 43 mg (71%) of Compound 96 was obtained from 128 mg (0.271 mmol) of Compound 24, 0.19 ml (2.7 mmol) of cyclopropylamine, and 0.88N HCl (AcOEt solution).

$^1$HNMR (DMSO-$d_6$) δ: 0.59–0.67 (m, 4H), 1.82–1.87 (m, 2H), 2.45–2.54 (m, 1H), 2.74–2.85 (m, 2H), 3.273 (s, 3H), 4.255 (s, 3H), 4.882 (t, 2H, J=7.4 Hz), 7.456 (dd, 2H, J=7.1 Hz, 8.1 Hz), 7.680 (ddd, 1H, J=1.2 Hz, 7.1 Hz, 8.3 Hz), 7.691 (ddd, 1H, J=1.2 Hz, 7.1 Hz, 8.3 Hz), 7.806 (d, 1H, J=8.3 Hz), 7.954 (d, 1H, J=8.3 Hz), 8.574 (br s, 2H), 9.151 (br d, 1H, J=8.1 Hz), 9.186 (br d, 1H, J=8.1 Hz).

Fab-MS (m/z): 451 $(M+1)^+$

EXAMPLE 77

Synthesis of Compound 97

In the same manner as in Example 30, 42 mg (69%) of Compound 97 was obtained from 56 mg (0.12 mmol) of a free base of Compound 96, 0.20 ml (2.3 mmol) of a 35% formaldehyde aqueous solution, 146 mg (2.33 mmol) of sodium cyanoborohydride, and 0.88N HCl (AcOEt solution).

$^1$HNMR (DMSO-$d_6$) δ: 0.60–0.69 (m, 2H), 0.76–0.86 (m, 2H), 1.94–2.14 (br s, 3H), 2.625 (d, 3H, J=4.9 Hz), 2.92–3.10 (m, 2H), 3.180 (s, 3H), 4.249 (s, 3H), 4.858 (t, 2H, J=7.7 Hz), 7.44 9 (ddd, 1H, J=1.0 Hz, 7.1 Hz, 8.1 Hz), 7.451 (ddd, 1H, J=1.0 Hz, 7.1 Hz, 8.1 Hz), 7.673 (ddd, 1H, J=1.1 Hz, 7.1 Hz, 8.2 Hz), 7.684 (ddd, 1H, J=1.2 Hz, 7.1 Hz, 8.3 Hz), 7.793 (br d, 1H, J=8.2 Hz), 7.963 (br d, 1H, J=8.3 Hz), 9.147 (br d, 1H, J=8.1 Hz), 9.186 (br d, 1H, J=8.1 Hz), 9.69–9.81 (br s, 1H).

Fab-MS (m/z): 465 $(M+1)^+$

EXAMPLE 78

Synthesis of Compound 98

In the same manner as in Example 24, 53 mg (79%) of Compound 98 was obtained from 123 mg (0.259 mmol) of Compound 24, 0.26 ml (2.6 mmol) of cyclopentylamine, and 0.88N HCl (AcOEt solution).

$^1$HNMR (DMSO-$d_6$) δ: 1.37–1.46 (m, 4H), 1.54–1.61 (m, 4H), 1.72–1.78 (m, 2H), 1.80–1.87 (m, 2H), 2.67–2.71 (m, 2H), 3.183 (s, 3H), 3.33–3.36 (m, 1H), 4.255 (s, 3H), 4.868 (t, 2H, J=7.6 Hz), 7.453 (dd, 2H, J=7.0 Hz, 7.9 Hz), 7.678 (ddd, 1H, J=1.2 Hz, 7.0 Hz, 8.2 Hz), 7.687 (ddd, 1H, J=1.2 Hz, 7.0 Hz, 8.2 Hz), 7.801 (d, 1H, J=8.2 Hz), 7.958 (d, 1H, J=8.2 Hz), 8.304 (br s, 2H), 9.147 (br d, 1H, J=7.9 Hz), 9.180 (dd, 1H, J=1.2 Hz, 7.9 Hz).

Fab-MS (m/z):479 $(M+1)^+$

EXAMPLE 79

Synthesis of Compound 99

In the same manner as in Example 30, 36 mg (62%) of Compound 99 was obtained from 52 mg (0.11 mmol) of a free base of Compound 98, 0.20 ml (2.3 mmol) of a 35% formaldehyde aqueous solution, 150 mg (2.39 mmol) of sodium cyanoborohydride, and 0.88N HCl (AcOEt solution).

$^1$HNMR (DMSO-$d_6$) δ: 1.32–1.79 (m, 8H), 1.92–2.00 (m, 2H), 2.478 (s, 3H), 2.66–2.81 (m, 2H), 3.191 (s, 3H), 3.33–3.36 (m, 1H), 4.249 (s, 3H), 4.82–4.92 (m, 2H), 7.453 (ddd, 1H, J=0.8 Hz, 7.0 Hz, 7.8 Hz), 7.458 (ddd, 1H, J=1.0 Hz, 7.1 Hz, 8.1 Hz), 7.682 (ddd, 1H, J=1.2 Hz, 7.0 Hz, 8.2 Hz), 7.688 (ddd, 1H, J=1.2 Hz, 7.1 Hz, 8.3 Hz), 7.804 (br d, 1H, J=8.2 Hz), 7.974 (br d, 1H, J=8.3 Hz), 9.148 (dd, 1H, J=1.2 Hz, 7.8 Hz), 9.185 (dd, 1H, J=1.2 Hz, 8.1 Hz), 9.59–9.72 (br s, 1H).

Fab-MS (m/z): 493 $(M+1)^+$

EXAMPLE 80

Synthesis of Compound 100

In the same manner as in Example 24, 97 mg (0.21 mmol) of Compound 24 was reacted with 0.42 ml (4.2 mmol) of butylamine to give 69 mg (73%) of a butylamino compound. In the same manner as in Example 30, 46 mg (65%) of Compound 100 was obtained from 66 mg (0.14 mmol) of the butylamino compound, 0.33 ml (3.8 mmol) of a 35% formaldehyde aqueous solution, 248 mg (3.96 mmol) of sodium cyanoborohydride, and 0.88N HCl (AcOEt solution).

$^1$HNMR (DMSO-$d_6$) δ: 0.754 (t, 3H, J=7.3 Hz), 1.04–1.14 (m, 2H), 1.23–1.32 (m, 2H), 1.95–1.99 (m, 2H), 2.72–2.79 (m, 4H), 3.185 (s, 3H), 4.244 (s, 3H), 4.862 (t, 2H, J=7.4 Hz), 7.43–7.48 (m, 2H), 7.678 (dd, 1H, J=7.1 Hz, 8.3 Hz), 7.686 (dd, 1H, J=7.1 Hz, 8.3 Hz), 7.796 (d, 1H, J=8.3 Hz), 7.960 (d, 1H, J=8.3 Hz), 9.147 (d, 1H, J=8.1 Hz), 9.184 (d, 1H, J=7.8 Hz), 9.579 (br s, 1H).

Fab-MS (m/z): 481 $(M+1)^+$

EXAMPLE 81

Synthesis of Compound 101

In the same manner as in Example 24, 103 mg (0.217 mmol) of Compound 24 was reacted with 0.42 ml (4.2 mmol) of isobutylamine to give 93 mg (92%) of an isobutylamino compound. In the same manner as in Example 30, 58 mg (58%) of Compound 101 was obtained from 91 mg (0.19 mmol) of the isobutylamino compound, 0.33 ml (3.8 mmol) of a 35% formaldehyde aqueous solution, 245 mg (3.90 mmol) of sodium cyanoborohydride, and 0.88N HCl (AcOEt solution).

$^1$HNMR (DMSO-$d_6$) δ: 0.702 (d, 3H, J=6.4 Hz), 0.722 (d, 3H, J=6.4 Hz), 1.55–1.64 (m, 1H), 1.93–2.00 (m, 2H), 2.60–2.64 (m, 2H), 2.65–2.80 (m, 2H), 3.191 (s, 3H), 4.244 (s, 3H), 4.863 (t, 2H, J=7.2 Hz), 7.454 (dd, 1H, J=7.0 Hz, 7.6 Hz), 7.461 (dd, 1H, J=7.3 Hz, 7.3 Hz), 7.683 (ddd, 1H, J=1.2 Hz, 7.0 Hz, 8.2 Hz), 7.689 (ddd, 1H, J=1.2 Hz, 7.3 Hz, 8.5 Hz), 7.801 (d, 1H, J=8.2 Hz), 7.962 (d, 1H, J=8.5 Hz), 9.065 (br s, 1H), 9.148 (br d, 1H, J=7.6 Hz), 9.184 (br d, 1H, J=7.3 Hz).

Fab-MS (m/z): 481 $(M+1)^+$

EXAMPLE 82

Synthesis of Compound 102

In the same manner as in Example 24, 97 mg (0.20 mmol) of Compound 24 was reacted with 0.49 ml (4.2 mmol) of isoamylamine to give 82 mg (84%) of an isoamylamino compound. In the same manner as in Example 30, 55 mg (63%) of Compound 102 was obtained from 78 mg (0.16 mmol) of the isoamylamino compound, 0.33 ml (3.8 mmol) of a 35% formaldehyde aqueous solution, 242 mg (3.85 mmol) of sodium cyanoborohydride, and 0.88N HCl (AcOEt solution).

$^1$HNMR (DMSO-$d_6$) δ: 0.712 (d, 3H, J=6.4 Hz), 0.717 (d, 3H, J=6.4 Hz), 1.10–1.21 (m, 2H), 1.31–1.39 (m, 2H), 1.90–1.95 (m, 2H), 2.65–2.79 (m, 4H), 3.187 (s, 3H), 4.245 (s, 3H), 4.872 (t, 2H, J=7.3 Hz), 7.43–7.48 (m, 2H), 7.678 (ddd, 1H, J=1.2 Hz, 7.0 Hz, 8.2 Hz), 7.687 (ddd, 1H, J=1.2 Hz, 7.0 Hz, 8.2 Hz), 7.797 (d, 1H, J=8.2 Hz), 7.960 (d, 1H, J=8.2 Hz), 9.147 (dd, 1H, J=1.2 Hz, 7.9 Hz), 9.186 (dd, 1H, J=1.2 Hz, 7.9 Hz), 9.551 (br s, 1H).

Fab-MS (m/z): 495 $(M+1)^+$

EXAMPLE 83

Synthesis of Compound 103

In the same manner as in Example 24, 98 mg (0.21 mmol) of Compound 24 was reacted with 0.49 ml (4.2 mmol) of 3-aminopentane to give 96 mg (97%) of a 3-pentylamino compound. In the same manner as in Example 30, 37 mg (35%) of Compound 103 was obtained from 94 mg (0.20 mmol) of the 3-pentylamino compound, 0.33 ml (3.8 mmol) of a 35% formaldehyde aqueous solution, 248 mg (3.95 mmol) of sodium cyanoborohydride, and 0.88N HCl (AcOEt solution).

$^1$HNMR (DMSO-$d_6$) δ: 0.731 (t, 3H, J=7.4 Hz), 0.763 (t, 3H, J=7.4 Hz), 1.28–1.38 (m, 2H), 1.41–1.52 (m, 2H), 1.90–2.00 (m, 2H), 2.4 60 (d, 3H, J=4.9 Hz), 2.76–2.84 (m, 3H), 3.191 (s, 3H), 4.250 (s, 3H), 4.850 (t, 2H, J=7.3 Hz), 7.455 (dd, 1H, J=7.1 Hz, 7.8 Hz), 7.461 (dd, 1H, J=7.3 Hz, 7.3 Hz), 7.688 (dd, 1H, J=7.1 Hz, 8.3 Hz), 7.691 (dd, 1H, J=7.3 Hz, 8.1 Hz), 7.803 (d, 1H, J=8.3 Hz), 7.965 (d, 1H, J=8.1 Hz), 8. 983 (br s, 1H), 9.148 (d, 1H, J=7.8 Hz), 9.185 (d, 1H, J=7.3 Hz).

Fab-MS (m/z): 495 $(M+1)^+$

EXAMPLE 84

Synthesis of Compound 104

In the same manner as in Example 24, 52 mg (68%) of Compound 104 was obtained from 71 mg (0.15 mmol) of Compound 24, 0.18 ml (1.5 mmol) of N-ethylpropylamine, and 0.88N HCl (AcOEt solution).

$^1$HNMR (DMSO-$d_6$) δ: 0.682 (t, 3H, J=7.3 Hz), 0.947 (t, 3H, J=7.3 Hz), 1.21–1.39 (m, 2H), 1.92–1.98 (m, 2H), 2.62–2.77 (m, 4H), 2.81–2.93 (m, 2H), 3.176 (s, 3H), 4.247 (s, 3H), 4.876 (t, 2H, J=7.3 Hz), 7.42–7.48 (m, 2H), 7.65–7.71 (m, 2H), 7.797 (d, 1H, J=8.1 Hz), 7.962 (d, 1H, J=8.3 Hz), 9.139 (dd, 1H, J=0.5 Hz, 8.1 Hz), 9.175 (dd, 1H, J=0.5 Hz, 8.1 Hz), 9.465 (br s, 1H).

Fab-MS (m/z): 481 $(M+1)^+$

EXAMPLE 85

Synthesis of Compound 105

In the same manner as in Example 30, 57 mg (56%) of Compound 105 was obtained from 94 mg (0.21 mmol) of a free base of Compound 94, 0.06 ml (1 mmol) of acetaldehyde, 65 mg (1.0 mmol) of sodium cyanoborohydride, and 0.88N HCl (AcOEt solution).

$^1$HNMR (DMSO-$d_6$) δ: 0.973 (t, 3H, J=7.3 Hz), 0.984 (d, 6H, J=6.7 Hz), 1.90–1.97 (m, 2H), 2.70–2.86 (m, 4H), 2.90–2.97 (m, 1H), 3.189 (s, 3H), 4.254 (s, 3H), 4.872 (t, 2H, J=7.4 Hz), 7.43–7.48 (m, 2H), 7.686 (ddd, 1H, J=1.2 Hz, 7.0 Hz, 8.2 Hz), 7.689 (ddd, 1H, J=1.2 Hz, 7.0 Hz, 8.2 Hz), 7.806 (d, 1H, J=8.2 Hz), 7.970 (d, 1H, J=8.2 Hz), 8.842 (br s, 1H), 9.149 (br d, 1H, J=7.6 Hz), 9.184 (br d, 1H, J=7.6 Hz).

Fab-MS (m/z): 481 $(M+1)^+$

EXAMPLE 86

Synthesis of Compound 106

In the same manner as in Example 24, 98 mg (0.21 mmol) of Compound 24 was reacted with 0.25 ml (4.1 mmol) of ethanolamine to give 73 mg (77%) of a hydroxyethylamino compound. In the same manner as in Example 30, 55 mg (69%) of Compound 106 was obtained from 70 mg (0.15 mmol) of the hydroxyethylamino compound, 0.33 ml (3.8 mmol) of a 35% formaldehyde aqueous solution, 239 mg (3.80 mmol) of sodium cyanoborohydride, and 0.88N HCl (AcOEt solution).

$^1$HNMR (DMSO-$d_6$) δ: 1.92–2.02 (m, 2H), 2.577 (s, 3H), 2.85–3.04 (m, 4H), 3.190 (s, 3H), 3.50–3.59 (m, 2H), 4.242 (s, 3H), 4. 834 (t, 2H, J=7.7 Hz), 5.186 (br s, 1H), 7.451 (ddd, 1H, J=1.0 Hz, 7.1 Hz, 8.1 Hz), 7.453 (ddd, 1H, J=1.0 Hz, 7.1 Hz, 8.1 Hz), 7.676 (ddd, 1H, J=1.2 Hz, 7.1 Hz, 8.3 Hz), 7.686 (ddd, 1H, J=1.2 Hz, 7.1 Hz, 8.3 Hz), 7.794 (br d, 1H, J=8.3 Hz), 7.953 (br d, 1H, J=8.3 Hz), 9.154 (br d, 1H, J=8.1 Hz), 9.189 (br d, 1H, J=8.1 Hz), 9.345 (br s, 1H ).

Fab-MS (m/z): 469 $(M+1)^+$

EXAMPLE 87

Synthesis of Compound 107

A mixture of 820 mg of Molecular Sieves 4A, 148 mg (0.640 mmol) of silver (I) oxide, 387 mg (0.940 mmol) of a-D-qlucopyranosylbromide tetraacetate, 143 mg (0.423 mmol) of known compound (F), and 13 ml of 1,2-dichloroethane was heated under reflux in an argon atmosphere for 3 hours. The reaction mixture was cooled to room temperature and filtered using Celite. The filtrate was diluted with water and extracted with dichloromethane. The extract was dried over anhydrous $MgSO_4$, and the solvent was evaporated. The residue was purified by silica gel column chromatography (toluene/AcOEt=8/1) to give 230 mg (81%) of an orthoester compound.

Fab-MS (m/z): 670 $(M+1)^+$

To a mixture of 197.6 mg of Molecular Sieves 4A, 157 mg (0.178 mmol) of the above-prepared orthoester compound, and 10 ml of 1,2-dichloroethane was added 0.0345 ml (0.178 mmol) of trimethylsilyl trifluoromethanesulfonate at −20° C. in an argon atmosphere, followed by stirring for 20 minutes. The reaction was stopped by addition of a saturated aqueous solution of sodium hydrogencarbonate. The reaction mixture was extracted with dichloromethane, and the extract was washed with brine and dried over anhydrous $MgSO_4$. The solvent was evaporated, and the residue was dissolved in a mixed solvent of 10 ml of chloroform and 15 ml of methanol, 98.3 mg (0.711 mmol) of potassium carbonate was added thereto, and the mixture was stirred at room temperature for 15 minutes. After adding two drops of concentrated hydrochloric acid to the reaction mixture, the solvent was removed by evaporation. The residue was purified by TLC ($CHCl_3$/MeOH=5/1) and triturated with an AcOEt/diisopropyl ether mixed solvent to yield 22 mg (32%) of Compound 107.

$^1$HNMR (DMSO-$d_6$) δ: 3.215 (s, 3H), 3.55–3.64 (m, 2H), 3.81–3.85 (m, 1H), 3.95–4.10 (m, 3H), 4.904 (d, 1H, J=5.4 Hz), 5.108 (d, 1H, J=5.1 Hz), 5.362 (d, 1H, J=4.9 Hz), 5.987 (t, 1H, J=4.0 Hz), 6.275 (d, 1H, J=8.6 Hz), 7.35–7.40 (m, 2H), 7.55–7.61 (m, 2H), 7.696 (d, 1H, J=8.1 Hz), 7.972 (d, 1H, J=8.8 Hz), 9.103 (d, 1H, J=8.1 Hz), 9.179 (dd, 1H, J=0.7 Hz, 8.1 Hz), 11.652 (s, 1H).

Fab-MS (m/z): 502 $(M+1)^+$

EXAMPLE 88

Synthesis of Compound 108

In the same manner as in Example 39, 122 mg (25%) of Compound 108 was obtained from 499 mg (0.942 mmol) of Compound 39, 4.32 g (13.8 mmol) of m-chloroperbenzoic acid, 1.16 g (13.8 mmol) of sodium hydrogencarbonate, 10 ml (97 mmol) of diethylamine, and 0.88N HCl (AcOEt solution).

$^1$HNMR (DMSO-$d_6$) δ: 0.942 (t, 6H, J=7.3 Hz), 1.81–1.88 (m, 2H), 2.69–2.73 (m, 2H), 2.82–2.90 (m, 4H), 3.174 (s, 3H), 4.118 (s, 3H), 4.734 (t, 2H, J=7.3 Hz), 7.127 (dd, 1H, J=2.4 Hz, 8.8 Hz), 7.141 (dd, 1H, J=2.4 Hz, 8.8 Hz), 7.575 (d, 1H, J=8.8 Hz), 7.737 (d, 1H, J=8.8 Hz), 8.554 (d, 1H, J=2.4 Hz), 8.587 (d, 1H, J=2.4 Hz), 9.358 (s, 1H), 9.400 (s, 1H), 9.437 (br s, 1H).

Fab-MS (m/z): 499 $(M+1)^+$

EXAMPLE 89

Synthesis of Compound 109

In 40 ml of THF was dissolved 408 mg (0.860 mmol) of Compound 24, and 464 mg (2.61 mmol) of N-bromosuccinimide was added thereto at 0° C., followed by stirring at room temperature overnight. The reaction was stopped by addition of a saturated aqueous solution off sodium hydrogensulfite, and the reaction mixture was extracted with trichloromethane. The extract was washed successively with a saturated aqueous solution of sodium hydrogencarbonate, water, and brine, and dried over anhydrous $MgSO_4$. The solvent was evaporated, and the residue was triturated with AcOEt under heating to give 522 mg (96%) of Compound 109.

$^1$HNMR ($CDCl_3$) δ: 2.00–2.05 (m, 2H), 2.891 (t, 2H, J=6.0 Hz), 3.274 (s, 3H), 4.210 (s, 3H), 4.894 (t, 2H, J=7.0 Hz), 7.428 (d, 1H, J=8.9 Hz), 7.484 (d, 1H, J=8.9 Hz), 7.704 (dd, 1H, J=2.1 Hz, 8.9 Hz), 7.727 (dd, 1H, J=2.1 Hz, 8.9 Hz), 9.420 (d, 1H, J=2.1 Hz), 9.445 (d, 1H, J=2.1 Hz).

Fab-MS (m/z): 630 $(M+1)^+$

EXAMPLE 90

Synthesis of Compound 110

In the same manner as in Example 24, 49 mg (75%) of Compound 110 was obtained from 520 mg (0.823 mmol) of Compound 109, 3.4 ml (32 mmol) of diethylamine, and 0.88N HCl (AcOEt solution).

$^1$HNMR (DMSO-$d_6$) δ: 0.973 (t, 6H, J=7.3 Hz), 1.87–1.96 (m, 2H), 2.78–2.84 (m, 2H), 2.85–2.94 (m, 4H), 3.135 (s, 3H), 4.261 (s, 3H), 4.856 (t, 2H, J=7.3 Hz), 7.78–7.84 (m, 3H), 7.963 (d, 1H, J=8.8 Hz), 9.270 (d, 1H, J=1.7 Hz), 9.303 (d, 1H, J=2.0 Hz).

Fab-MS (m/z): 625 $(M+1)^+$

EXAMPLE 91

Injections

In 20 l of ethanol was dissolved 2.0 g of Compound 92, and the solution was filtered under pressure through Millipore Filter (pore size: 0.22 μm) for sterilization. The resulting sterile filtrate was put into brown vials in 5.0 ml portions and then lyophilized in a conventional manner to obtain lyophilized preparations weighing 0.5 mg per vial.

EXAMPLE 92

Tablets

Tablets were prepared in a conventional manner from 180 mg of Compound 92, 90 mg of lactose, 40 mg of corn starch, 4 mg of polyvinyl alcohol, 28 mg of Avicel, and 1 mg of magnesium stearate.

REFERENCE EXAMPLE 1

Preparation of Compound 80

In a mixture of 0.25 ml of trifluoroacetic acid and 0.025 ml of 3N hydrochloric acid was dissolved 50 mg (0.1 mmol) of known Compound (E), followed by stirring at room temperature for 1 day. The reaction mixture was poured into 10 ml of ice-water, and the resulting precipitate thus formed was collected by filtration and purified by preparative TLC (2% MeOH/$CHCl_3$) to give 12 mg (38%) of Compound 80.

$^1$HNMR (DMSO-$d_6$) δ: 3.263 (s, 3H), 5.401 (s, 2H), 7.205–7.795 (m, 6H), 8.036 (d, 1H, J=7.9 Hz), 9.236 (d, 1H, J=8.1 Hz), 11.322 (s, 1H), 11.489 (s, 1H).

Fab-MS (m/z): 326 $(M+1)^+$

REFERENCE EXAMPLE 2

Preparation of Compound 81

In the same manner as in Example 1, 135 mg (58%) of known Compound 81 was obtained from 208 mg (0.61 mmol) of Compound (F), 74 mg (1.8 mmol) of sodium hydride, and 0.063 ml (0.73 mmol) of allyl bromide.

$^1$HNMR ($CDCl_3$-DMSO-$d_6$, 10/1) δ: 3.04 (s, 3H), 4.80–5.20 (m, 4H), 6.16 (m, 1H), 7.28–7.64 (m, 6H), 9.18 (d, 1H, J=8 Hz), 9.20 (d, 1H, J=8 Hz), 9.86 (s, 1H).

EIMS (m/z): 379 $(M)^+$

REFERENCE EXAMPLE 3

Preparation of Compound 82

In the same manner as in Example 1, 60 mg (72%) of Compound 82 was obtained from 70 mg (0.2 mmol) of known Compound (F), 32 mg (0.8 mmol) of sodium hydride, and 0.06 ml (0.6 mmol) of allyl bromide.

$^1$HNMR (DMSO-$d_6$) δ: 3.176 (s, 3H), 5.122 (m, 4H), 5.256 (dd, 2H, J=1.3, 17.3 Hz), 5.371 (dd, 2H, J=1.3, 10.6 Hz), 6.144 (m, 2H), 7.421–7.661 (m, 6H), 9.188 (dd, 1H, J=1.0, 7.9 Hz).

EIMS (m/z): 419 $(M)^+$

REFERENCE EXAMPLE 4

Preparation of Compound 83

In a mixed solvent of 7 ml of THF and 0.5 ml of pyridine was dissolved 145 mg (0.38 mmol) of Compound 81, and 4 ml of a pyridine solution of 200 mg (0.76 mmol) of osmium tetroxide was added thereto, followed by stirring at room temperature for 6 hours. To the reaction mixture were added 7 ml of water, 7 ml of pyridine, and 348 mg (3.4 mmol) of sodium thiosulfate, followed by stirring for 1 hour. $CHCl_3$ was added to the reaction mixture, and the organic layer was separated, washed with brine, and dried over $MgSO_4$. The solvent was evaporated, and the residue was purified by silica gel column chromatography ($MeOH/CHCl_3$=1/9) to give 93 mg (59%) of Compound 83.

$^1$HNMR (DMSO-$d_6$) δ: 3.186 (s, 3H), 3.620–3.643 (m, 2H), 4.805 (dd, 1H, J=7.9, 15.6 Hz), 4.956 (dd , 1H, J=3.16, 15.6 Hz), 5.407 (d, 1H, J=4.9 Hz), 5.480 (t, 1H, J=5.2 Hz), 7.351–7.818 (m, 6H), 9.094 (d, 1H, J=7.9 Hz), 9.131 (d, 1H, J=7.9 Hz), 11.736 (s, 1H).

Fab-MS (m/z): 413 $(M)^+$

REFERENCE EXAMPLE 5

Preparation of Compound 84

In the same manner as in Reference Example 4, 21 mg (34%) of Compound 84 was prepared from 53 mg (0.13 mmol) of Compound 82 and 64 mg (0.25 mmol) of osmium tetroxide.

$^1$HNMR (DMSO-$d_6$) δ:2.965 (t, 2H, J=5.6 Hz), 3.139 (m, 2H), 3.196 (s, 1.5H), 3.198 (s, 1.5H), 3.622 (m, 2H), 4.259 (d, 1H, J=5.3 Hz), 4.406 (d, 1H, J=5.5 Hz), 4.514 (t, 1H, J=5.5 Hz), 4.640 (t, 1H, J=5.7 Hz), 4.675 (dd, 1H, J=9.0, 14.8 Hz), 4.727 (dd, 1H, J=8.1, 14.8 Hz), 4.886 (dd, 1H, J=4.5, 14.8 Hz), 4.928 (dd, 1H, J=8.1, 14.9 Hz), 7.399 (t, 2H, J=7.2 Hz), 7.612 (t, 2H, J=7.1 Hz), 7.828 (t, 2H, J=8.7 Hz), 9.142 (d, 2H, J=7.9 Hz).

Fab-MS (m/z): 488 $(M+1)^+$

REFERENCE EXAMPLE 6

Preparation of Compound 85

In 30 ml of THF was dissolved 215 mg (0.38 mmol) of Compound 66, and 24 ml of 4N sulfuric acid was added thereto, followed by stirring at 60° C. overnight. After cooling to room temperature, ice was added to the reaction mixture, and the mixture was extracted with AcOEt. The extract was washed with water and then with brine and dried over $MgSO_4$. The solvent was evaporated, and the residue was purified by silica gel column chromatography (AcOEt/toluene=1/2) to give 107 mg (59%) of Compound 85.

$^1$HNMR ($CDCl_3$) δ: 1.310 t, 3H, J=7.2 Hz), 1.329 (t, 3H, J=7.2 Hz), 4.331 (q, 2H, J=7.2 Hz), 4.338 (q, 2H, J=7.2 Hz), 4.953 (s, 2H), 5.037 (s, 2H), 5.170 (s, 2H), 6.424 (brs, 1H), 7.288 (d, 1H, J=8.1 Hz), 7.362 (d, 1H, J=8.2 Hz), 7.37–7.42 (m, 2H), 7.49–7.55 (m, 2H), 7.869 (d, 1H, J=7.7 Hz), 9.441 (d, 1H, J=7.8 Hz).

Fab-MS (m/z): 484 $(M+1)^+$

REFERENCE EXAMPLE 7

Preparation of Compound 86

In the same manner as in Example 6, 34 mg (39%) of Compound 86 was obtained from 105 mg (0.21 mmol) of Compound 61.

$^1$HNMR (DMSO-$d_6$) δ: 1.59–1.65 (m, 2H), 1.70–1.82 (m, 2H), 3.03–3.27 (m, 2H), 3.09–3.14 (m, 2H), 4.371 (t, 1H, J=5.0 Hz), 4.419 (t, 1H, J=5.0 Hz), 4.780 (t, 2H, J=7.3 Hz), 4.818 (t, 2H, J=7.4 Hz), 4.972 (s, 2H), 7.288 (ddd, 1H, J=0.8 Hz, 7.0 Hz, 7.8 Hz), 7.370 (t, 1H, J=7.2 Hz), 7.501 (ddd, 1H, J=1.2, 7.0, 8.2 Hz), 7.563 (ddd, 1H, J=1.1, 7.2, 8.3 Hz), 7.779 (d, 1H, J=8.3 Hz), 7.848 (d, 1H, J=8.2 Hz), 8.043 (d, 1H, J=7.2 Hz), 9.412 (dd, 1H, J=0.8, 7.8 Hz).

Fab-MS (m/z): 428 $(M+1)^+$

REFERENCE EXAMPLE 8

Preparation of Compound 87

In the same manner as in Reference Example 6, 267 mg (58%) of Compound 87 was obtained as a 3:1 mixture of regioisomers from 574 mg (1.31 mmol) of Compound 68.

$^1$HNMR (DMSO-$d_6$) δ: 3.5–3.6 (br, 1H), 3.945 (t, 2H, J=5.4 Hz), 4.960 (s, 2H), 4.972 (t, 2H, J=5.4 Hz), 7.20–7.35 (m, 2H), 7.40–7.54 (m, 2H), 7.70–7.82 (m, 2H), 8.042 (d, 1H, J=7.8 Hz), 8.443 (s, 0.25H), 8.467 (s, 0.75H), 9.324 (d, 0.75H, J=8.0 Hz), 9.369 (d, 0.25H, J=7.3 Hz), 11.422 (s, 0.75H), 11.587 (s, 0.25H).

Fab-MS (m/z): 356 $(M+1)^+$

REFERENCE EXAMPLE 9

Preparation of Compound 88

In 10 ml of DMF was dissolved 179 mg (0.39 mmol) of one of the regioisomers of Compound 63, in which $R^3$ is hydrogen, and 310 mg (1.18 mmol) of triphenylphosphine and 0.060 ml (1.2 mmol) of bromine were added to the solution at 0° C. in an argon atmosphere, followed by stirring at room temperature for 3 hours. Water was added to the reaction mixture to stop the reaction, and the reaction mixture was extracted with AcOEt. The extract was washed successively with water and brine, and dried over $MgSO_4$. The solvent was evaporated, and the residue was purified by silica gel column chromatography (AcOEt/toluene=1/8). The purified product was dissolved in 5 ml of DMF, and 0.045 ml (0.52 mmol) of morpholine was added thereto, followed by stirring at 80° C. for one day in an argon atmosphere. Ice-water was added to the reaction mixture, and the resulting precipitate was collected by filtration, dried under reduced pressure, and purified by TLC ($CHCl_3$/MeOH=25/1). In the same manner as in Reference Example 4, THP was removed, and the residue was dissolved in a mixed solvent of $CHCl_3$ and AcOEt, 0.88N HCl (AcOEt solution) was added thereto, followed by stirring at room temperature for 1 hour. The resulting precipitate was collected by filtration, washed with AcOEt, and dried under reduced pressure to give 35 mg (19%) of Compound 88.

$^1$HNMR (DMSO-$d_6$) δ: 2.29–2.34 (m, 2H), 2.96–3.04 (m, 2H), 3.30–3.40 (m, 4H), 3.66–3.72 (m, 2H), 3.56–3.90 (m, 2H), 4.972 (s, 2H), 5.093 (t, 2H, J=7.1 Hz), 7.245 (ddd, 1H, J=0.9, 7.0, 7.9 Hz), 7.370 (dd, 1H, J=7.0, 7.9 Hz), 7.458 (ddd, 1H, J=1.2, 7.0, 8.2 Hz), 7.565 (ddd, 1H, J=1.2, 7.0, 8.2 Hz), 7.799 (d, 1H, J=8.2 Hz), 7.884 (d, 1H, J=8.2 Hz), 8.071 (d, 1H, J=7.9 Hz), 8.516 (s, 1H), 9.345 (d, 1H, J=7.9 Hz), 10.4–10.6 (br, 1H), 11.823 (s, 1H).

Fab-MS (m/z): 439 $(M+1)^+$

As has been fully described, the present invention provides a therapeutic agent for thrombocytopenia useful as a medicine and a novel indolocarbazole derivative useful as an active ingredient of the therapeutic agent.

While the invention has been described in detail and with reference to specific examples thereof, it will be apparent to one skilled in the art that various changes and modifications can be made therein without departing from the spirit and scope thereof.

What is claimed is:

1. A method of treating thrombocytopenia comprising administering, to a patient suffering from thrombocytopenia, an effective amount of an indolocarbazole derivative represented by the formula (I):

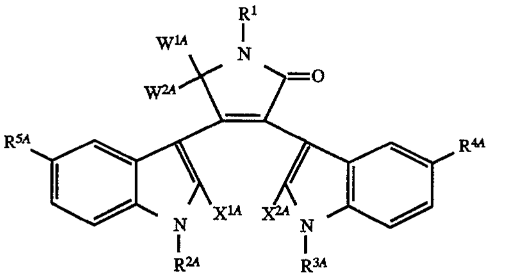

(I)

wherein $R^1$ represents a hydrogen atom; a substituted or unsubstituted lower alkyl group, a substituted or unsubstituted aralkyl group or a tetrahydropyranyl group; $R^{2A}$ and $R^{3A}$, which may be the same or different, each represent a hydrogen atom, a substituted or unsubstituted lower alkyl group, a lower alkenyl group, or a substituted or unsubstituted aralkyl group; $R^{4A}$ and $R^{5A}$, which may be the same or different, each represent a hydrogen atom, a formyl group, a hydroxyl group or a halogen atom; $W^{1A}$ and $W^{2A}$ represent hydrogen atom or combine together to represent oxygen atom; and $X^{1A}$ and $X^{2A}$ represent hydrogen atom or combine together to represent a single bond, or a pharmaceutically acceptable salt thereof, provided that when $X^A$ forms a single bond, then $R^1$, $R^{2A}$, $R^{3A}$, $R^{4A}$, $R^{5A}$, and $W^{1A}$ and $W^{2A}$ do not simultaneously represent a hydrogen atom.

2. An indolocarbazole derivative represented by the formula (II):

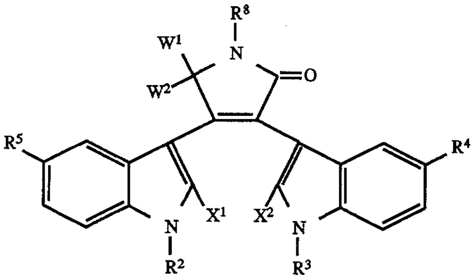

(II)

wherein $R^8$ represents a substituted or unsubstituted lower alkyl group, a substituted or unsubstituted aralkyl group or a tetrahydropyranyl group; $R^2$ and $R^3$ which may be the same or different, each represent a hydrogen atom, a substituted or unsubstituted lower alkyl group, a lower alkenyl group, or a substituted or unsubstituted aralkyl group; $R^4$ and $R^5$, which may be the same or different, each represent a hydrogen atom, a formyl group, a hydroxyl group or a halogen atom; $W^1$ and $W^2$ represent hydrogen atom or combine together to represent oxygen atom; and $X^1$ and $X^2$ represent hydrogen atom or combine together to represent a single bond, or a pharmaceutically acceptable salt thereof, provided that $R^2$ and $R^3$ do not simultaneously represent a hydrogen atom, and also provided that when $R^2$ and $R^3$, which may be the same or different, each represent an allyl group or $CH_2CH(OH)CH_2OH$, then $R^8$ is not a methyl group and $W^1$ and $W^2$ are not combined to represent an oxygen atom.

3. The compound as claimed in claim 2, wherein $R^8$ is a substituted or unsubstituted lower alkyl group.

4. The compound as claimed in claim 3, wherein $R^8$ is a methyl group.

5. The compound as claimed in any of claims 2 to 4, wherein $R^2$ and $R^3$, which may be the same or different, is a substituted or unsubstituted lower alkyl group.

6. The compound as claimed in any of claims 2 to 4, wherein X forms a single bond.

7. The compound as claimed in claim 5, wherein X forms a single bond.

* * * * *

UNITED STATES PATENT AND TRADEMARK OFFICE

CERTIFICATE OF CORRECTION

PATENT NO. : 5,629,304

DATED : May 13, 1997

INVENTOR(S) : CHIKARA MURAKATA ET AL.

It is certified that error appears in the above-identified patent and that said Letters Patent is hereby corrected as shown below:

ON TITLE PAGE, IN THE ABSTRACT

Line 18, "represents" should read --represent--.

COLUMN 1

Line 27, "Indolocarbozole" should read --Indolocarbazole--;

Line 39, "Indolocarbozole" should read --Indolocarbazole--.

COLUMN 2

Line 3, "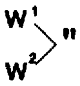" should read --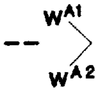--.

Line 9, "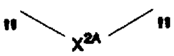" should read --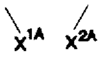--.

COLUMN 4

Line 36, "wiley" should read --Wiley--.

COLUMN 5

Line 16, "$W^1$" (second occurrence) should read --$X^1$--;

Line 42, "east" should read --least--.

COLUMN 11

Compound 16, "$H_2$" hould read --H,H--;

UNITED STATES PATENT AND TRADEMARK OFFICE
CERTIFICATE OF CORRECTION

PATENT NO. : 5,629,304

DATED : May 13, 1997

INVENTOR(S) : CHIKARA MURAKATA ET AL.

It is certified that error appears in the above-identified patent and that said Letters Patent is hereby corrected as shown below:

COLUMN 14
Table 1-continued "X" should --$X^1$,$X^2$--.

COLUMN 16 Table 1-continued
Compound 53, "HCl" should be deleted;
"X" should read --$X^1$,$X^2$--.

COLUMN 17
Line 37, "be low" should read --below--.

COLUMN 19
Line 19, "were" should read --the test compounds were--;
Line 20, "the test compounds" should be deleted.

COLUMN 20
Line 38, "a" should be deleted.

COLUMN 22
Line 42, "4.67 6" should read --4.676--.

UNITED STATES PATENT AND TRADEMARK OFFICE

CERTIFICATE OF CORRECTION

PATENT NO. : 5,629,304

DATED : May 13, 1997

INVENTOR(S) : CHIKARA MURAKATA ET AL. Page 3 of 3

It is certified that error appears in the above-identified patent and that said Letters Patent is hereby corrected as shown below:

COLUMN 35
Line 23, "of" (first occurrence) should be deleted.

COLUMN 41
Line 8, "63" should read --69--.

COLUMN 48
Line 47, "qlucopyranosylbromide" should read --glucopyranosylbromide--.

COLUMN 54
Line 15, "$R^3$" should read --$R^3$,--.

Signed and Sealed this

Fourteenth Day of April, 1998

Attest:

BRUCE LEHMAN

*Attesting Officer* *Commissioner of Patents and Trademarks*